US010208326B2

(12) United States Patent
Jensen

(10) Patent No.: US 10,208,326 B2
(45) Date of Patent: Feb. 19, 2019

(54) METHODS AND MATERIALS FOR BIOSYNTHESIS OF MANOYL OXIDE

(71) Applicant: Evolva SA, Reinach (CH)

(72) Inventor: Niels Bjerg Jensen, Kastrup (DK)

(73) Assignee: EVOLVA SA, Reinach (CH)

( * ) Notice: Subject to any disclaimer, the term of this patent is extended or adjusted under 35 U.S.C. 154(b) by 0 days.

(21) Appl. No.: 15/523,868

(22) PCT Filed: Nov. 13, 2015

(86) PCT No.: PCT/EP2015/076595
§ 371 (c)(1),
(2) Date: May 2, 2017

(87) PCT Pub. No.: WO2016/075302
PCT Pub. Date: May 19, 2016

(65) Prior Publication Data
US 2017/0314049 A1  Nov. 2, 2017

(30) Foreign Application Priority Data

Nov. 13, 2014  (DK) ................................. 2014 70694

(51) Int. Cl.

| C12P 17/06 | (2006.01) |
| C12N 9/88 | (2006.01) |
| C12P 5/00 | (2006.01) |
| C12P 17/04 | (2006.01) |
| C07D 307/92 | (2006.01) |
| C07D 311/92 | (2006.01) |
| C12N 9/10 | (2006.01) |

(52) U.S. Cl.
CPC ............ *C12P 17/06* (2013.01); *C07D 307/92* (2013.01); *C07D 311/92* (2013.01); *C12N 9/1085* (2013.01); *C12N 9/88* (2013.01); *C12P 5/007* (2013.01); *C12P 17/04* (2013.01); *C12Y 205/01029* (2013.01); *C12Y 402/03* (2013.01); *C12Y 402/03025* (2013.01)

(58) Field of Classification Search
CPC .... C12P 5/007; C12Y 205/01029; C12N 9/88
USPC ...................................................... 435/252.3
See application file for complete search history.

(56) References Cited

U.S. PATENT DOCUMENTS

| 5,204,253 A | 4/1993 | Sanford et al. |
| 5,538,880 A | 7/1996 | Lundquist et al. |
| 6,013,863 A | 1/2000 | Lundquist et al. |
| 6,329,571 B1 | 12/2001 | Hiei |
| 2003/0148479 A1 | 8/2003 | Keasling et al. |
| 2006/0014264 A1 | 1/2006 | Sauer et al. |
| 2008/0281135 A1 | 11/2008 | Tissier et al. |
| 2014/0073020 A1 | 3/2014 | Park et al. |

FOREIGN PATENT DOCUMENTS

| CN | 101 475 946 | 7/2009 |
| CN | 101 538 576 | 9/2009 |
| CN | 102 676 549 | 9/2012 |
| CN | 103695441 | 4/2014 |
| DE | 10 2009 025996 | 12/2010 |
| DK | 201400056 | 4/2014 |
| WO | WO2009044336 | 4/2009 |
| WO | WO2009101126 | 8/2009 |
| WO | WO2009140394 | 11/2009 |
| WO | WO2011153378 | 12/2011 |
| WO | WO2013075239 | 5/2013 |
| WO | WO2015091943 | 6/2015 |
| WO | WO 2015/104553 | 7/2015 |
| WO | WO2015113569 | 8/2015 |
| WO | WO2015113570 | 8/2015 |
| WO | WO2015184553 | 12/2015 |
| WO | WO2015197075 | 12/2015 |
| WO | WO2016070885 | 5/2016 |
| WO | WO2016075302 | 5/2016 |
| WO | WO2016107920 | 7/2016 |

OTHER PUBLICATIONS

Pateraki et al. (Plant Physiology, Mar. 1, 2014, vol. 164, pp. 1222-1236), 2014.*
Ageitos, et al., "Oily yeasts as oleaginous cell factories", Appl. Microbiol Biotechnol., 90:1219-1227 (2011).
Altschul, et al., "Basic Local Alignment Search Tool", J Mol Biol, 215:403-10 (1990).
Andersen-Ranberg, "Identification and characterization of biosynthetic parts involved in plant diterpenoid biosynthesess", University of Copenhagen I Center for Synthetic Biology, Abstract of PhD thesis (Jun. 24, 2014), pp. 1-2.
Andersen-Ranberg, et al., "Expanding the molecular diversity through synthetic biology: Using combinatorial biochemistry for reconstruction of pathways to high-value and novel diterpenes", TERPNET 2013 (11th international meeting on biosynthesis, function and biotechnology of isoprenoids in terrestrial and marine organisms); Book of Abstracts, 2013.
Asada, et al., "Labdane-type diterpenoids from hairy root cultures of Coleus forskohlii, possible intermediates in the biosynthesis of forskolin", Phytochemistry, 79:141-146 (2012).
Asadollahi, et al., "Enhancement of farnesyl diphosphate pool as direct precursor of sesquiterpenes through metabolic engineering of the mevalonate pathway in *Saccharomyces cerevisiae*", Biotechnology and Bioengineering, 106:86-96 (2010).
Ausubel, et al., "Current Protocols in Molecular Biology". (2003).
Azuma, et al., Floral scent emissions from *Asarum yaeyamense* and related species:, Biochemical Systematics and Ecology, 38:548-553 (2010).

(Continued)

*Primary Examiner* — Tekchand Saidha
(74) *Attorney, Agent, or Firm* — McDonnell Boehnen Hulbert & Berghoff LLP

(57) ABSTRACT

The invention relates to recombinant microorganisms and methods for producing manoyl oxide.

15 Claims, 4 Drawing Sheets
Specification includes a Sequence Listing.

(56) References Cited

OTHER PUBLICATIONS

Bankar, et al., "Environmental and industrial applications of Yarrowia lipolytica", Appl Microbiol Biotechnol., 84:847-865 (2009).
Bateman,et al., "Pfam 3:1:1313 multiple alignments and profile HMMs match the majority of proteins", Nucleic Acid Research, 27:260-262 (2009).
Beopoulos, et al., "Yarrowia lipolytica: A method and a tool to understand the mechanism implicated in lipid accumulation", Biochimie, 91:692-696 (2009).
Bomm, et al., "Rearranged (4-2)-abeo-cleodane and clerodane diterpenes from Aristolochia chamissonis", Phytochemistry, 50:455-461(1999).
Bozic, et al., "Towards Elucidating Carnosic Acid Biosynthesis in Lamiaceae: Functional Characterization of the Three First Steps of the Pathway in Salvia fruticosa and Rosmarinus officinalis", PLOS ONE, 10:e0124106, pp. 1-28 (2015).
Bruckner, et al., "High-level diterpene production by transient expression in Nicotiana benthamiana", Plant Methods, 9:1-10 (2013).
Cambie, et al., "Conversion of 8a,13-EPOXYLABD-14-ENE Into a Compound With an Ambergris-Type Odour", Austrialian Journal of Chemistry, 24:583-591 (1971).
Caniard, et al., "Discovery and functional characterization of two diterpene synthases for sclareol biosynthesis in *Salvia sclarea* (L.) and their relevance for perfume manufacture", BMC Plant Biology, 12:1-13 (2012).
Chenna, et al., "Multiple sequence alignment with the Clustal Series of programs" Nucleic Acid Research, 31:3497-3500 (2003).
Cui, et al., "Candidate genes involved in tanshinone biosynthesis in hairy roots ofSalvia miltiorrhiza revealed by eDNA microarray", Molecular Biology Reports, 38: 2471-2478 (2011).
Delpech, et al., "Total Synthesis of Forskolin—Part II#" Tetrahedron Letters, 37:1019-1022 (1996).
Demetzos et al., "A simple and rapid method for the differentiation of C-13 manoyl oxide epimers in biologically important samples using GC-MS analysis supported with NMR spectroscopy and computational chemistry results", Bioorganic & Medicinal Chemistry Letters, 12:3605-3609 (2002).
Donald, et al., "Effects of overproduction of the catalytic domain of 3-hydroxy-3-methylglutaryl coezyme A reductase on squalene synthesis in *Saccharomyces cerevisiae*", Applied and Environmental Microbiology, 63:3341-3344 (1997).
Dueholm, et al., "Evolution of substrate recognition sites(SRSs) in cytochromes P450 from Apiaceae exemplified by the CYP71AJ" BMC Evolutionary Biology, 15:122., pp. 1-14 (2015).
El-Awaad, et al., "Bifunctional CYP81AA proteins catalyse identical hydroxylations but alternative regioselective phenol couplings in plant xanthone biosynthesis," Nature Communications, 7:11472, pp. 1-12 (2016).
Englund, et al., "Metabolic Engineering of *Synechocystis* sp. PCC 6803 for Production of the Plant Diterpenoid Manoyl Oxide", ACS Synthetic Biology, 4:1270-1278 (2015).
Falara, et al., "The Tomato Terpene Synthase Gene Family", Plant Physiology, 157:770-789 (2011).
Fang, et al., "Generation of expressed sequence tags from a eDNA library of Coleusforskohliifor identification of genes involved in terpene biosynthesis", Biologia Plantarum, 59:463-468 (2015).
Fokialkakis, et al., "Antileishmanial activity of natural diterpenes from *Cistus* sp. And semisynthetic derivatives thereof", Bio Pharm Bull, 29:1775-1778. (2008).
Forman, et al., "Diterpene decorating properties of native and engineered CYP76AH enzymes from *Lamiaceae* species", University of Copenhagen, Faculty of Science (2016).
Frija, et al., "Isolation, chemical, and biotransformation routes of labdane-type-diterpenes", Chemical Reviews, 111:4418-4452 (2011).
Gabetta, et al., "Minor Diterpenoids of Coleus Forskolii", Phytochemistry, 28:859-862 (1989).
Garcia-Granados et al., "Manoyl-oxide biotransformations with filamentousfungi", Current Organic Chemistry, 11:679-692 (2007).
Giaever, et al., "The yeast deletion collection: a decade of functional genomics", Genetics, 197:451-465 (2014).
Godard, et al., "Body composition and hormonal adaptations associated with forskolin consumption in overweight and obese men" Obesity Research, 13:1335-1343 (2005).
Gong, et al., "Diterpene Synthases and Their Responsible Cyclic Natural Products", Natural Products and Bioprosecting, 4:59-72 (2014).
Gossen, et al., "Studying gene function in eukaryotes by condiational gene inactivation", Annu Rev Genet, 36:153-73 (2002).
Gotoh, "Substrate Recognition Sites in Cytochrome P450 Family 2 (CYPB) Proteins Inferred from Comparative Analyses of Amino Acid and Coding Nucleotide Sequences", The Journal of Biological Chemistry, 267:83-90 (1992).
Green & Sambrook, "Molecular Cloning:A laboratory Manual", fourth Edition. (2012).
Gricman, et al., "Identification of universal selectivity—determining positions in cytochrome P450 monooxygenases by systematic sequence-based literature mining", Proteins 83:1593-1603 (2015).
Gunnewich et al., "A diterpene synthase from the clary sage Salvia sclarea catalyzes the cyclization of geranylgeranyl diphosphate to (8R)-hydroxy-copalyl diphosphate", Phytochemistry, 91:93-99 (2013).
Guo, et al., "CYP76AH1 catalyzes turnover of miltiradiene in tanshinones biosynthesis and enables heterologous production of ferruginol in yeasts", PNAS, 110:12108-12113 (2013).
Guo, et al., "Cytochrome P450 promiscuity leads to a bifurcating biosynthetic pathway for tanshinones", New Phytologist, 210:525-534 (2016).
Hamberger et al., "Plant P450s as versatile drivers for evolution of species-specific chemical diversity", Philosophical Transaction of the Royal Society B, 368(1612):20120426 (2013).
Hansen, et al., "Evolutionary cues from functional switching of two closely related class II diterpene synthases", 53rd Annual Meeting of the Phytochemical Society of North America; Aug. 9-13, 2014, Raleigh. NorthCarolina.
Harde et al., "Extraction of forskolin from Coleus forskohlii roots using three phase partitioning", Separation and Purification Technology, 96:20-25 (2012).
Janocha, et al., "Design and characterization of an efficient CYP105A1-based whole-cell biocatalyst for the conversion of resin acid diterpenoids in permeabilized*Escherichia coli*", Applied Microbiology Biotechnology, 97:7639-7649 (2013).
Karlin et al., "Applications and statistics for multiple high-scoring segments in molecular sequenes", Proc. Natl. Acad. Sci., 90:5873-7. (1993).
Karlin, et al., "Methods for assessing the statistical significance of molecular sequence features by using general scoring schemes", Proc. Natl. Acad. Sci., 87:2264-2268. (Mar. 1990).
Kennedy, et al., "Positive and negative regulation of squalene synthase (ERG9), an ergosterol biosynthetic gene, in *Saccharomyces cerevisae*", Biochimica et Biophysica Acta, 1517:177-89. (2001).
Khoury, et al., "Computational design of Candida boidinii xylose reductase for altered cofactor specificity", Protein Science, 18:2125-2138. (2009).
Kikura, et al., "Pharmacokinetics and a simulation model of colforsin daropate, new forskolin derivative inotropic vasodilator, in patients undergoing coronary artery bypass grafting" Pharmacological Research, 49: 275-281 (2004).
King et al., "Production of Bioactive Diterpenoids in the Euphorbiaceae Depends on Evolutionarily Conserved Gene Clusters", The Plant Cell, 26:3286-3298 (2014).
Kirby et al., "Cloning of casbene and neocembrene synthases from *Euphorbiaceae* plants and expression in *Saccharomyces cerevisiae*", Phytochemistry, 71:1466-1473 (2010).
Kristoffersen, "BIOFORS (Elucidation of forskolin biosynthetic pathway in Coleusforskohlii)", BIOFORS Report Summary (European Union) Report from the University of Copenhagen, Aug. 5, 2015, pp. 1-2.
Li, et al., "High-density cultivation of oleaginous yeast Rhodosporiduium toruloides Y4 in fed-batch culture," Enzyme and Microbial Technology,41:312-7 (2007).

(56) References Cited

OTHER PUBLICATIONS

Matsingou, et al., "Effect of the nature of the 3beta-substitution in manoyl oxides on the thermotrophic behavior of DPPC lipid bilayer and on DPPC liposomes", Journal of Liposome Research, 17:89-105 (2007).
Mattanovich, et al., "Recombinant protein production in yeasts", Methods in Molecular Biology, 824:329-358 (2012).
Mikkelsen, et al., "Microbial production of indolyglucosinolate through engineering of multi-gene pathway in a versatile yeast expression platform", Metabolic Engineering, 14:104-111 (2012).
Mitchell, Rod, "Identification and characterization of diterpene synthases in the salvinorin A biosynthetic pathway", A Thesis Submitted to the Faculty of Graduate Studies, Degree of Master of Science, Department of Biological Sciences, The University of Calgary, Alberta, Aug. 2012 (185 pages).
Mukherjee, et al., "Enhanced forskolin production in genetically transformed cultures of Coleus forskohlii by casein hydrolysate and studies on growth and organisation", Biotechnology Letters, 22:133-136 (2000).
Nelson et al., "A P450-centric view of plant evolution", The Plant Journal 66:194-211 (2011).
Nicaud, "Yarrowia lipolytica", Yeast, 29:409-418 (2012).
Nielsen, et al., "Microbial synthesis of the forskolin precursor manoyl oxide in enantiomerically pure form", Applied and Environmental Microbiology, 80:7258-7265 (2014).
Nour-Eldin, et al., "User cloning and User fusion:the ideal cloning techniques for small and big laboratories", Methods in Molecular Biology, 643:185-200 (2010).
Oikawa, et al., "Cloning and functional expression of cDNA encoding aphidicolan-16 beta-ol synthase:a key enzyme responsible for formation of an unsual diterpene skeleton in biosynthesis of aphidicolin", Journal American Chemical Society, 123:5154-5. (2001).
Osmani, et al., "Substrate specificity of plant UDP-dependent glycosyltransferase predicted from crystal structures and homology modeling", Phytochemistry, 70:325-347 (2009).
Pateraki,et al., "Manoyl Oxide (13R), the Biosynthetic Precursor of Forskolin, is Synthesized in Specialized Root Cork Cells in Coleus forskohlii," Plant Physiology, 164:1222-1236 (2014).
Pateraki, et al., "Manoyl oxide as a precursor for forskolin biosynthesis: identification and characterization of the involved biosynthetic enzymes from Coleus forskohlii", TERPNET 2013 (11th international meeting on biosynthesis, function and biotechnology of isoprenoids in terrestrial and marine organisms); Book of Abstracts (2013).
Pattanaik, et al., "Terpenoids and Their Biosynthesis in Cyanobacteria", Life, 5:269-293 (2015).
Piirainen, et al., "Glycoengineering of yeasts from the perspective of glycosylation efficiency", New Biotechnology, 31:532-537 (2014).
Podust, et al., "Diversity of P450 enzymes in the biosynthesis of natural products", Natural Products Reports, 29:1251-1266 (2012).
Prelich, Gregory, "Gene Overexpression: Uses, mechanisms, and Interpretation" Genetics, 190:841-854 (2012).
Saenge, et al., "Potential use of oleaginous red yeast Rhodotorula glutinis for the bioconversion of crude glycerol from biodiesel plant to lipids and carotenoids", Process Biochemistry, 46:210-218 (2011).
Sainsbury, et al., "Using a Virus-Derived System to Manipulate Plant Natural Product Biosynthetic Pathways", Methods Enzymology, 517:185-202 (2012).
Sawada, et al., "Multiple mutagenesis of P450 isoflavonoid synthase reveals a key active-site residue," Biochemical and Biophysical Research Communications, 330:907-913 (2005).
Schalk, et al., "A single amino acid substitution (F363I) converts the regiochemistry of the spearmint (-)-limonene hydroxylase from a C6- to a C3-hydroxylase," PNAS, 97:11948-11953 (2000).
Schalk, et al., Toward a Biosynthetic Route to Sclareol and Amber Odorants, Journal of the American Chemical Society, 134:18900-18903 (2012).
Schuler, et al., "Functional Genomics of P450s", Annu Rev Plant Biol, 54:629-67 (2003).
Seifert, et al., "Identification of selectivity-determining residues in cytochrome P450 monooxygenases: a systematic analysis of the substrate recognition site 5", Proteins 74:1028-1035 (2009).
Sonnhammer, et al., Pfam: A Comprehensive Database of Protein Domain Families Based on Seed Alignments:, Proteins, 28:405-420 (1997).
Sonnhammer, et al., "Pfam:multiple sequence alignments and HMM-profiles of protein domains" Nucleic Acids Research, 26:320-322 (1998).
Spanner, et al., "High-Throughput Testing of Terpenoid Biosynthesis Candidate Genes Using Transient Expression in Nicotiana benthamiana", Methods in Molecular Biology, 1153:245-255 (2014).
Suzuki,et al., "Identification and characterization of a novel anthocyanin malonyltransferase fromscarlet sage (Salvia splendens) flowers:an enzyme that is phylogenetically separated from other anthocyanin acyltransferases", The Plant Journal, 38:994-1003 (2004).
Takahashi, et al., "Functional Characterization of Premnaspirodiene Oxygenase, a Cytochrome P450 Catalyzing Regio- and Stereo-specific Hydroxylations of Diverse Sesquiterpene Substrates", The Journal of Biological Chemistry, 282:31744-31754 (2007).
Tatusova, et al., Blast 2 sequences—a new tool for comparing protein and nucleotide sequences; FEMS Microbiology Letters, 174:247-250 (1999).
Thompson, et al., "CLUSTAL W: improving the sensitivity of progressive multiple sequence alignment through sequence weighting, positions-specific gap penalties and weight matrix choice", Nucleic Acids Research, 22:4673-4680 (1994).
Toporkova, et al., "Determinants governing the CYP74 catalysis: conversion of allene oxide synthase into hydroperoxide lyase by site-directed mutagenesis," FEBS Lett. 582:3423-3428 (2008).
Van Ooyen et al., "Heterologous protein production in the yeast Kluyveromyces lactis", FEMS Yeast Res. 6(3):381-92 (2006).
The Arabidopsis Genome Initiative, "Analysis of the genome sequence of the flowering plant Arabidopsis thaliana" Nature, 408(6814):796-815. (2000).
Voinnet, et al., "An enhanced transient expression system in plants based on suppression of gene silencing by the p19 protein of tomato bushy stunt virus," The Plant Journal, 33:949-956 (2003).
Wagh, et al., "Forskolin: Upcoming antiglaucoma molecule", Journal of Postgraduate Medicine, 58:199-202 (2012).
Wiley Registry of Mass Spectral Data, 8th Edition, Jul. 2006, John Wiley & Sons, ISBN: 978-0-470-04785-9.
Xu, et al., "Generation of hepatitis B virus Pre S2-S antigen in Hnsenulapolymorpha", Virologica Sinica, 29:403-409 (2014).
Yousif, et al., "Forskolin reverses tachyphylaxis to the bronchodilator effects of salbutamol: an in-vitro study on isolated guinea-pig trachea", J Pharm Pharmacol, 51:181-186 (1999).
Zerbe, et al., "Bifunctional cis-abienol synthase from Abies balsamea discovered by transcriptome sequencing and its implications for diterpenoid fragrance production", The Journal of Biological Chemistry, 287:12121-12131 (2012).
Zerbe, et al., "Gene Discovery of Modular Diterpene Metabolism in Nonmodel Systems", Plant Physiology, 162:1073-1091 (2013).
Zhou, et al., "Modular Pathway Engineering of Diterpenoid Synthases and the Mevalonic Acid Pathway for Miltiradiene Production", Journal of the American Chemical Society,134: 3234-3241 (2012).
Zhu, et al., "A multi-omic map of the lipid producing yeast Rhodosporidum toruloides", Nature Communications, 3:1-11 (2012).
GenBank Accession No. CfTPS1.
GenBank Accession No. CfTPS2.
GenBank Accession No. CfTPS3.
GenBank Accession No. CfTPS4.
GenBank Accession No. CfTPS15.
GenBank Accession No. KF444506.
GenBank Accession No. KF444507.
GenBank Accession No. KF444508.
GenBank Accession No. KF444509.
GenBank Accession No. KF471011.
GenBank Accession No. ALE19959.
GenBank Accession No. ALE19960.
GenBank Accession No. NKH477.
GenBank Accession No. KP337687.1.
GenBank Accession No. AJQ30187.1.

(56) References Cited

OTHER PUBLICATIONS

GenBank Accession No. AJQ30188.1.
GenBank Accession No. KP091843.1.
GenBank Accession No. KP091844.1.
Genseq Accession No. AWL79394.
Geneseq Accession No. AXT35994.
GenBank ABC98596-1 GenID 86553638.
GenBank AAC16897-1 GeneID 3150037.
GenBank ABB88839-2 GeneID 93211213.
International Search Report and Written Opinion issued by the International Searching Authority for International Application No. PCT/EP2015/076595, dated Feb. 8, 2016 (15 pages).
International Search Report and Written Opinion issued by the International Searching Authority for International Application No. PCT/EP2014/078728 dated Mar. 6, 2015 (15 pages).
Restriction Requirement in U.S. Appl. No. 15/103,838; dated Jan. 11, 2017 pp. 1-6.
Response to Restriction Requirement in U.S. Appl. No. 15/103,838 dated Mar. 13, 2017 pp. 1-7.
International Search Report and Written Opinion issued by the International Searching Authority for International Application No. PCT/DK2015/050181 dated Oct. 12, 2015 (16 pages).
International Search Report and Written Opinion issued by the International Searching Authority for International Application No. PCT/DK2015/050021 dated Aug. 25, 2015 (18 pages).
International Preliminary Report on Patentability issued in the International Application No. PCT/DK2015/050021 dated Aug. 2, 2016 (10 pages).
International Search Report and Written Opinion issued by the International Searching Authority for International Application No. PCT/DK2015/050020 dated Apr. 30, 2015 (13 pages).
International Preliminary Report on Patentability issued in the International Application No. PCT/DK2015/050020 dated Jan. 15, 2016 (19 pages).
International Search Report issued by the International Searching Authority for International Application No. PCT/DK2015/050337 dated Feb. 5, 2016 (7 pages).
Written Opinion issued in the International Application No. PCT/DK2015/050337 dated Feb. 5, 2016 (8 pages).
International Search Report and Written Opinion issued by the International Searching Authority for International Application No. PCT/EP2015/081457, dated Mar. 9, 2016 (19 pages).
Cambie et al., "Conversion of Manoyl Oxide into 12 β-Hydroxymanoyl Oxide," Australian Journal of Chemistry, 44:469-75. (1991).
Innis et al., "Optimization of PCRs", PCR Protocols: A Guide to Methods and Applications. (1990).
Medini et al., "Antibacterial activity and phytochemical composition of leaf and berry essential oils of two *Juniperus phoenicea* subspecies gathered in Tunisia," Journal of Exp Bio and Agri Sciences 1(3):166-73. (2013).
Examination Report issued by the European Patent Office for European Application No. 14816252.2, dated Mar. 27, 2017 (7 pages).
Ignea, et al., "Production of the forksolin precursor 11β-hydroxyl-manoyl oxide in yeast using surrogate enzymatic activities," Microbial Cell Factors, 15:46, pp. 1-11 (2016).
Ignea, et al., "Reconstructing the chemical diversity of labdane-type diterpenebiosynthesis in yeast," Metabolic Engineering, 28:91-103 (2014).
Cambie et al., "Conversion of manoyl oxide into 12-beta-hydroxymanoyl oxide", Aust. J. Chem., 44:469-475 (1991).
UniProt Accession No. R9UNPO dated Sep. 18, 2013, pp. 1-4.
UniProt Accession No. R9UPX6 dated Sep. 18, 2013, pp. 1-4.
UniProt Accession No. R9UM66 dated Sep. 18, 2013, pp. 1-4.

International Preliminary Report on Patentability issued by the International Searching Authority for International Application No. PCT/EP2015/076595, dated May 26, 2017 (10 pages).
International Search Report and Written Opinion issued by the International Searching Authority for International Application No. PCT/EP2016/058270, dated Jun. 23, 2016 (16 pages).
Extended European Search Report and Opinion issued by the European Patent Office for European Application No. 15706365.2, dated Jun. 19, 2017 (8 pages).
International Preliminary Report on Patentability issued in the International Application No. PCT/EP2015/081457, dated Jul. 4, 2017 (12 pages).
Medini et al., "Antibacterial activity and pytochemical composition of leaf and berry essential oils of two *Juniperus phoenicea* subspecies gathered in Tunisia", Journal of Exp. Biology and Agric. Sciences., 1(3): 166-173 (Jul. 2013).
UniProt Accession No. R9UM66 (KC702394), dated Sep. 18, 2013 (4 pages).
UniProt Accession No. R9UNP0 (KC702396), dated Sep. 18, 2013 (4 pages).
UniProt Accession No. R9UPX6 (KC702395), dated Sep. 18, 2013 (4 pages).
GenBank Accession No. CfTPS1, dated Apr. 9, 2014 (2 pages).
GenBank Accession No. CfTPS2, dated Apr. 9, 2014 (2 pages).
GenBank Accession No. CfTPS3, dated Apr. 9, 2014 (2 pages).
GenBank Accession No. CfTPS4, dated Apr. 9, 2014 (2 pages).
GenBank Accession No. CfTPS15, dated Apr. 9, 2014 (2 pages).
SenBank Accession No. KF444506, dated Apr. 9, 2014 (2 pages).
SenBank Accession No. KF444507, dated Apr. 9, 2014 (2 pages).
SenBank Accession No. KF444508, dated Apr. 9, 2014 (2 pages).
SenBank Accession No. KF444509, dated Apr. 9, 2014 (2 pages).
SenBank Accession No. KF471011, dated Apr. 9, 2014 (2 pages).
SenBank Accession No. ALE19959, dated Sep. 20, 2015 (2 pages).
SenBank Accession No. ALE19960, dated Sep. 20, 2015 (2 pages).
SenBank Accession No. NKH477, dated Sep. 11, 2016 (6 pages).
SenBank Accession No. KP337687.1, dated Jan. 14, 2015 (2 pages).
SenBank Accession No. AJQ30187.1, dated Jun. 11, 2015 (2 pages).
SenBank Accession No. AJQ30188.1, dated Jun. 11, 2015 (2 pages).
GenBank Accession No. KP091843.1, dated Jun. 11, 2015 (2 pages).
GenBank Accession No. KP091844.1, dated Jun. 11, 2015 (2 pages).
Genseq Accession No. AWL79394, dated Jun. 11, 2009 (4 pages).
Geneseq Accession No. AXT35994, dated Feb. 4, 2010 (2 pages).
GenBank ABC98596-1 GenID 86553638, dated Jan. 31, 2014 (2 pages).
GenBank AAC16897-1 GeneID 3150037, dated Jul. 25, 2016 (2 pages).
GenBank ABB88839-2 GeneID 93211213, dated May 28, 2008 (2 pages).
Carmichael et al., "Geotrichum candidum," Mycologia, 49(6):820-830 (1957).
Guo et al., "Protein tolerance to random amino acid change", Proceedings of the National Academy of Sciences USA, vol. 101, No. 25, pp. 9205-9210 (2004).
Mastromarino et al., "Bacterial vaginosis: a review on clinical trials with probiotics," New Microbiolgica, 36:229-238 (2013).
Papini et al., "Scheffersomyces stipitis: a comparative systems biology study with the Crabtree positive yeast *Saccharomyces cerevisiae*," Microbial Cell Factories, 11:136 (2012).
Hoffman et al., "An Ancient Yeast for Young Geneticists: A Primer on the Schizosaccharomyces pombe Model System," Genetics 201(2):403-23 (2015).
Forskalin from Sigma-Aldrich PubChem SID 24278035, dated Mar. 30, 2007 (pp. 1-6).

\* cited by examiner (13R) Manoyloxide

Ambrox

Manoyloxide

Forskolin

SEQUENCE LISTING

<160> NUMBER OF SEQ ID NOS: 12

<210> SEQ ID NO 1
<211> LENGTH: 894
<212> TYPE: DNA
<213> ORGANISM: Artificial sequence
<220> FEATURE:
<223> OTHER INFORMATION: Sequence encoding GGPPS7 of Synechococcus - codon optimized for expression in S. cerevisiae

<400> SEQUENCE: 1

```
atggtcgcac aaactttcaa cctggatacc tacttatccc aaagacaaca acaagttgaa       60
gaggccctaa gtgctgctct tgtgccagct tatcctgaga gaatatacga agctatgaga      120
tactcccctcc tggcaggtgg caaaagatta agacctatct tatgtttagc tgcttgcgaa      180
ttggcaggtg gttctgttga acaagccatg ccaactgcgt gtgcacttga aatgatccat      240
acaatgtcac taattcatga tgacctgcca gccatggata cgatgatttt cagaagagga      300
aagccaacta atcacaaggt gttcggggaa gatatagcca tcttagcggg tgatgcgctt      360
ttagcttacg ctttgaaca tattgcttct caaacaagag gagtaccacc tcaattggtg      420
ctacaagtta ttgctagaat cggacacgcc gttgctgcaa caggcctcgt tggaggccaa      480
```

```
gtcgtagacc ttgaatctga aggtaaagct atttccttag aaacattgga gtatattcac    540
tcacataaga ctggagcctt gctggaagca tcagttgtct caggcggtat tctcgcaggg    600
gcagatgaag agcttttggc cagattgtct cattacgcta gagatatagg cttggctttt    660
caaatcgtcg atgatatcct ggatgttact gctacatctg aacagttggg gaaaaccgct    720
ggtaaagacc aggcagccgc aaaggcaact tatccaagtc tattgggttt agaagcctct    780
agacagaaag cggaagagtt gattcaatct gctaaggaag ccttaagacc ttacggttca    840
caagcagagc cactcctagc gctggcagac ttcatcacac gtcgtcagca ttaa          894
```

<210> SEQ ID NO 2
<211> LENGTH: 297
<212> TYPE: PRT
<213> ORGANISM: Synechococcus
<400> SEQUENCE: 2

```
Met Val Ala Gln Thr Phe Asn Leu Asp Thr Tyr Leu Ser Gln Arg Gln
1               5                   10                  15

Gln Gln Val Glu Glu Ala Leu Ser Ala Ala Leu Val Pro Ala Tyr Pro
            20                  25                  30

Glu Arg Ile Tyr Glu Ala Met Arg Tyr Ser Leu Ala Gly Gly Lys
        35                  40                  45

Arg Leu Arg Pro Ile Leu Cys Leu Ala Ala Cys Glu Leu Ala Gly Gly
50                  55                  60

Ser Val Glu Gln Ala Met Pro Thr Ala Cys Ala Leu Glu Met Ile His
65                  70                  75                  80

Thr Met Ser Leu Ile His Asp Asp Leu Pro Ala Met Asp Asn Asp Asp
                85                  90                  95

Phe Arg Arg Gly Lys Pro Thr Asn His Lys Val Phe Gly Glu Asp Ile
            100                 105                 110

Ala Ile Leu Ala Gly Asp Ala Leu Leu Ala Tyr Ala Phe Glu His Ile
        115                 120                 125

Ala Ser Gln Thr Arg Gly Val Pro Pro Gln Leu Val Leu Gln Val Ile
130                 135                 140

Ala Arg Ile Gly His Ala Val Ala Ala Thr Gly Leu Val Gly Gly Gln
145                 150                 155                 160

Val Val Asp Leu Glu Ser Glu Gly Lys Ala Ile Ser Leu Glu Thr Leu
                165                 170                 175

Glu Tyr Ile His Ser His Lys Thr Gly Ala Leu Leu Glu Ala Ser Val
            180                 185                 190

Val Ser Gly Gly Ile Leu Ala Gly Ala Asp Glu Glu Leu Leu Ala Arg
        195                 200                 205

Leu Ser His Tyr Ala Arg Asp Ile Gly Leu Ala Phe Gln Ile Val Asp
210                 215                 220

Asp Ile Leu Asp Val Thr Ala Thr Ser Glu Gln Leu Gly Lys Thr Ala
225                 230                 235                 240

Gly Lys Asp Gln Ala Ala Ala Lys Ala Thr Tyr Pro Ser Leu Leu Gly
                245                 250                 255

Leu Glu Ala Ser Arg Gln Lys Ala Glu Glu Leu Ile Gln Ser Ala Lys
            260                 265                 270

Glu Ala Leu Arg Pro Tyr Gly Ser Gln Ala Glu Pro Leu Leu Ala Leu
        275                 280                 285

Ala Asp Phe Ile Thr Arg Arg Gln His
    290                 295
```

<210> SEQ ID NO 3
<211> LENGTH: 1191
<212> TYPE: DNA
<213> ORGANISM: Artificial sequence
<220> FEATURE:
<223> OTHER INFORMATION: Sequence encoding GGPPS10 of Aspergillus
      nidulans - codon optimized for expression in S. cerevisiae

<400> SEQUENCE: 3

```
atgacgtccg attcgcactt tcaccctccg cacgcaatac cacccaggat tagctccaac      60
cgaatgtcag gtgcatctac tcgagacaag gcagcactaa tgggaaactt cgagaaggac     120
tggctgtcaa aggtgacaag cttcagaca aacaccgatt tgtctaaaag acacacgcga      180
aatcagtcaa gtctcgacgg gacaaaatac aaagatggga atggtccca agagaatgag     240
gaggtgatca tgggtccgta cgactacatg ctgcaacacc cggggaagga cctgcgacgg     300
cagatgatca acgcttttaa cgtatggttg aaggtgccat ctgagagcct ggccatcatc     360
accaaagtag tggctatgct ccataccgct tcattattga tcgacgacgt cgaagacaac     420
tctcttctcc ggcgaggaat tccggtcgca catagcatct atggcaccgc gcagacgatc     480
aattcggcaa actacgtta cttcctcgcc ctccaggagg tgcaaaaact gaagagtccg     540
gcagctatcg acatatacgt ccaggagctg ctgaatttac acagagggca aggcatggat     600
ctgttctggc gagacacgct cacttgtcca agcgaagatg aatacttgga gatggtgggc     660
aacaagactg gaggtttgtt ccggctagct gtgaaattga tgcaagctga aagcagcact     720
ggaaaggact gtgtggccct tgtgaatgtt tgggactgg tctttcagat atgcgacgac     780
tatctcaatt tatccgacac gacgtatacc cagaacaaag gctctgtga agacctcaca     840
gagggcaaat tttcattccc cattatccac agcattcgat cgaacccggg gaaccatcag     900
ctcatcaata tcctccggca gagaacaaag gatgaagaag tcaaacgcta cgcgctccag     960
tatatggaaa gcacgggcag tttcaagcat acgcaggatg ttgttcggca gctacgtgcc    1020
agagctctgc agctcattga agagattgag aacagcgaaa atggcgagca accggaggaa    1080
cacaatgacg gtacgatggt ccgggcaatc ctcgataaaa tcacagaatc caccttggct    1140
gatacgaata cgactacgag agatatcaac ggcaactgtg cgaccccgtta a            1191
```

<210> SEQ ID NO 4
<211> LENGTH: 396
<212> TYPE: PRT
<213> ORGANISM: Aspergillus nidulans

<400> SEQUENCE: 4

```
Met Thr Ser Asp Ser His Phe His Pro Pro His Ala Ile Pro Pro Arg
1               5                   10                  15

Ile Ser Ser Asn Arg Met Ser Gly Ala Ser Thr Arg Asp Lys Ala Ala
            20                  25                  30

Leu Met Gly Asn Phe Glu Lys Asp Trp Leu Ser Lys Gly Asp Lys Leu
        35                  40                  45

Gln Thr Asn Thr Asp Leu Ser Lys Arg His Thr Arg Asn Gln Ser Ser
    50                  55                  60

Leu Asp Gly Thr Lys Tyr Lys Asp Gly Lys Trp Ser Gln Glu Asn Glu
65                  70                  75                  80

Glu Val Ile Met Gly Pro Tyr Asp Tyr Met Leu Gln His Pro Gly Lys
                85                  90                  95

Asp Leu Arg Arg Gln Met Ile Asn Ala Phe Asn Val Trp Leu Lys Val
            100                 105                 110
```

```
Pro Ser Glu Ser Leu Ala Ile Ile Thr Lys Val Val Ala Met Leu His
        115                 120                 125
Thr Ala Ser Leu Leu Ile Asp Asp Val Glu Asp Asn Ser Leu Leu Arg
    130                 135                 140
Arg Gly Ile Pro Val Ala His Ser Ile Tyr Gly Thr Ala Gln Thr Ile
145                 150                 155                 160
Asn Ser Ala Asn Tyr Val Tyr Phe Leu Ala Leu Gln Glu Val Gln Lys
                165                 170                 175
Leu Lys Ser Pro Ala Ala Ile Asp Ile Tyr Val Gln Glu Leu Leu Asn
            180                 185                 190
Leu His Arg Gly Gln Gly Met Asp Leu Phe Trp Arg Asp Thr Leu Thr
        195                 200                 205
Cys Pro Ser Glu Asp Glu Tyr Leu Glu Met Val Gly Asn Lys Thr Gly
    210                 215                 220
Gly Leu Phe Arg Leu Ala Val Lys Leu Met Gln Ala Glu Ser Ser Thr
225                 230                 235                 240
Gly Lys Asp Cys Val Ala Leu Val Asn Val Leu Gly Leu Val Phe Gln
                245                 250                 255
Ile Cys Asp Asp Tyr Leu Asn Leu Ser Asp Thr Thr Tyr Thr Gln Asn
            260                 265                 270
Lys Gly Leu Cys Glu Asp Leu Thr Glu Gly Lys Phe Ser Phe Pro Ile
        275                 280                 285
Ile His Ser Ile Arg Ser Asn Pro Gly Asn His Gln Leu Ile Asn Ile
    290                 295                 300
Leu Arg Gln Arg Thr Lys Asp Glu Glu Val Lys Arg Tyr Ala Leu Gln
305                 310                 315                 320
Tyr Met Glu Ser Thr Gly Ser Phe Lys His Thr Gln Asp Val Val Arg
                325                 330                 335
Gln Leu Arg Ala Arg Ala Leu Gln Leu Ile Glu Glu Ile Glu Asn Ser
            340                 345                 350
Glu Asn Gly Glu Gln Pro Glu His Asn Asp Gly Thr Met Val Arg
        355                 360                 365
Ala Ile Leu Asp Lys Ile Thr Glu Ser Thr Leu Ala Asp Thr Asn Thr
    370                 375                 380
Thr Thr Arg Asp Ile Asn Gly Asn Cys Ala Thr Arg
385                 390                 395
```

<210> SEQ ID NO 5
<211> LENGTH: 2196
<212> TYPE: DNA
<213> ORGANISM: Artificial sequence
<220> FEATURE:
<223> OTHER INFORMATION: cDNA encoding Coleus forskohlii TPS2

<400> SEQUENCE: 5

```
atgagtcgag ttgcaagtct ggatgcgttg aatggaattc aaaaagtcgg cccagccacc        60
attgggactc ctgaagagga aaataaaaag attgaggatt ccattgagta cgtgaaggag       120
ttgttgaaga caatgggcga cgggcgaatc agcgtttccc cgtacgacac agcaatagtt       180
gccctgatta aggacttgga aggaggtgat ggaccagagt ttccatcttg tctagagtgg       240
attgcacaga tcaactggc tgatggttct tgggggatc acttcttctg tatttatgat       300
cgggttgtta atacagcagc ttgtgtggtc gccttaaagt cgtggaacgt tcacgcagac       360
aagattgaga aggagcagt gtacctgaag gagaatgtgc ataaacttaa agatgggaag       420
```

-continued

```
attgagcaca tgcccgcagg gtttgaattt gtggttcctg ccactcttga aagagccaaa    480
gccttgggga tcaaaggtct tccctatgat gatcctttca tcagggaaat ttatagtgca    540
aaacaaacaa gattgaccaa gataccaaag gcatgatct  acgaatctcc aacttcttta    600
ttatatagtt tagacggtct ggaaggcttg gagtgggaca agatactgaa actgcagtcg    660
gccgatggct cattcatcac ctctgtgtcg tctactgcct tcgtattcat gcacaccaac    720
gaccttaaat gccacgcctt catcaaaaat gccctcacca attgcaacgg ggagtaccc     780
cacacgtatc cagtggatat cttcgcacga ctttgggcag tggaccgact gcaacgcctc    840
ggaatatctc gattctttga gcctgagatc aaatatttaa tggatcacat caataacgtg    900
tggagggaga agggagtttt cagttcaagg cattcacaat ttgcggatat tgacgacaca    960
tccatgggca tcaggcttct gaaaatgcac ggatacaatg tcaacccaaa tgcacttgaa   1020
catttcaaac agaaagatgg gaagtttaca tgctatgctg atcaacatat cgagtctcca   1080
tcccccatgt acaatctcta cagggctgct cagcttcgtt ttccaggaga agaaattctt   1140
caacaagccc ttcaatttgc ctataatttt ctacatgaaa acctagccag caatcacttt   1200
caagaaaaat gggtcatatc cgaccaccta attgatgagg taaggatcgg gctgaagatg   1260
ccatggtacg ccaccctacc gcgagtggag gcttcatact atcttcaaca ttatggtgga   1320
tccagcgacg tatggattgg caaaacttta tacagaatgc cagaaatcag taacgacaca   1380
tacaaaatac ttgcacaatt ggacttcaac aaatgtcaag cacaacatca gttggaatgg   1440
atgtccatga agagtggta tcaaagtaat aatgttaaag aatttgggat aagcaagaaa   1500
gaacttcttc ttgcttactt tttggctgct gcaaccatgt ttgaacccga acgcacacaa   1560
gagaggatta tgtgggcgaa aactcaagtc gtttctcgga tgatcacatc atttctcaac   1620
aaagaaaaca caatgtcatt cgacctaaag attgcacttt taacccaacc ccaacatcaa   1680
ataaatggtt ctgagatgaa gaatggactt gctcaaactc ttcctgcagc cttccgacaa   1740
ctactcaagg aattcgacaa atacacaaga catcaattga ggaatacttg gaacaaatgg   1800
ttgatgaaac tgaagcaagg agatgacaat ggcggcgcag atgcagagct ccttgcaaac   1860
acattaaaca tatgtgctgg acataacgaa gacatatatt cgcactatga atacaccgct   1920
ctctcctccc tcacaaacaa aatatgtcag cgtctaagtc aaattcaaga taaaaagatg   1980
ctggaaattg aggaggggag cataaaagat aaggagatgg agctcgaaat acaaacattg   2040
gtgaagttag tcctccaaga aaccagtggg ggtatcgata gaaacatcaa gcaaacattt   2100
ttatcagtat tcaagacatt ttactacagg gcctaccacg atgctaagac tatcgatgcc   2160
catattttcc aagtactatt tgaaccagtg gtctga                            2196
```

<210> SEQ ID NO 6
<211> LENGTH: 731
<212> TYPE: PRT
<213> ORGANISM: Coleus forskohlii

<400> SEQUENCE: 6

Met Ser Arg Val Ala Ser Leu Asp Ala Leu Asn Gly Ile Gln Lys Val
1               5                   10                  15

Gly Pro Ala Thr Ile Gly Thr Pro Glu Glu Glu Asn Lys Lys Ile Glu
            20                  25                  30

Asp Ser Ile Glu Tyr Val Lys Glu Leu Leu Lys Thr Met Gly Asp Gly
        35                  40                  45

Arg Ile Ser Val Ser Pro Tyr Asp Thr Ala Ile Val Ala Leu Ile Lys
    50                  55                  60

```
Asp Leu Glu Gly Gly Asp Gly Pro Glu Phe Pro Ser Cys Leu Glu Trp
 65                  70                  75                  80

Ile Ala Gln Asn Gln Leu Ala Asp Gly Ser Trp Gly Asp His Phe Phe
                 85                  90                  95

Cys Ile Tyr Asp Arg Val Val Asn Thr Ala Ala Cys Val Val Ala Leu
            100                 105                 110

Lys Ser Trp Asn Val His Ala Asp Lys Ile Glu Lys Gly Ala Val Tyr
        115                 120                 125

Leu Lys Glu Asn Val His Lys Leu Lys Asp Gly Lys Ile Glu His Met
    130                 135                 140

Pro Ala Gly Phe Glu Phe Val Val Pro Ala Thr Leu Glu Arg Ala Lys
145                 150                 155                 160

Ala Leu Gly Ile Lys Gly Leu Pro Tyr Asp Asp Pro Phe Ile Arg Glu
                165                 170                 175

Ile Tyr Ser Ala Lys Gln Thr Arg Leu Thr Lys Ile Pro Lys Gly Met
            180                 185                 190

Ile Tyr Glu Ser Pro Thr Ser Leu Leu Tyr Ser Leu Asp Gly Leu Glu
        195                 200                 205

Gly Leu Glu Trp Asp Lys Ile Leu Lys Leu Gln Ser Ala Asp Gly Ser
    210                 215                 220

Phe Ile Thr Ser Val Ser Ser Thr Ala Phe Val Phe Met His Thr Asn
225                 230                 235                 240

Asp Leu Lys Cys His Ala Phe Ile Lys Asn Ala Leu Thr Asn Cys Asn
                245                 250                 255

Gly Gly Val Pro His Thr Tyr Pro Val Asp Ile Phe Ala Arg Leu Trp
            260                 265                 270

Ala Val Asp Arg Leu Gln Arg Leu Gly Ile Ser Arg Phe Phe Glu Pro
        275                 280                 285

Glu Ile Lys Tyr Leu Met Asp His Ile Asn Asn Val Trp Arg Glu Lys
    290                 295                 300

Gly Val Phe Ser Ser Arg His Ser Gln Phe Ala Asp Ile Asp Asp Thr
305                 310                 315                 320

Ser Met Gly Ile Arg Leu Leu Lys Met His Gly Tyr Asn Val Asn Pro
                325                 330                 335

Asn Ala Leu Glu His Phe Lys Gln Lys Asp Gly Lys Phe Thr Cys Tyr
            340                 345                 350

Ala Asp Gln His Ile Glu Ser Pro Ser Pro Met Tyr Asn Leu Tyr Arg
        355                 360                 365

Ala Ala Gln Leu Arg Phe Pro Gly Glu Glu Ile Leu Gln Gln Ala Leu
    370                 375                 380

Gln Phe Ala Tyr Asn Phe Leu His Glu Asn Leu Ala Ser Asn His Phe
385                 390                 395                 400

Gln Glu Lys Trp Val Ile Ser Asp His Leu Ile Asp Glu Val Arg Ile
                405                 410                 415

Gly Leu Lys Met Pro Trp Tyr Ala Thr Leu Pro Arg Val Glu Ala Ser
            420                 425                 430

Tyr Tyr Leu Gln His Tyr Gly Gly Ser Ser Asp Val Trp Ile Gly Lys
        435                 440                 445

Thr Leu Tyr Arg Met Pro Glu Ile Ser Asn Asp Thr Tyr Lys Ile Leu
    450                 455                 460

Ala Gln Leu Asp Phe Asn Lys Cys Gln Ala Gln His Gln Leu Glu Trp
465                 470                 475                 480
```

```
Met Ser Met Lys Glu Trp Tyr Gln Ser Asn Val Lys Glu Phe Gly
                485                 490                 495

Ile Ser Lys Lys Glu Leu Leu Leu Ala Tyr Phe Leu Ala Ala Thr
            500                 505                 510

Met Phe Glu Pro Glu Arg Thr Gln Glu Arg Ile Met Trp Ala Lys Thr
        515                 520                 525

Gln Val Val Ser Arg Met Ile Thr Ser Phe Leu Asn Lys Glu Asn Thr
    530                 535                 540

Met Ser Phe Asp Leu Lys Ile Ala Leu Leu Thr Gln Pro Gln His Gln
545                 550                 555                 560

Ile Asn Gly Ser Glu Met Lys Asn Gly Leu Ala Gln Thr Leu Pro Ala
                565                 570                 575

Ala Phe Arg Gln Leu Leu Lys Glu Phe Asp Lys Tyr Thr Arg His Gln
            580                 585                 590

Leu Arg Asn Thr Trp Asn Lys Trp Leu Met Lys Leu Lys Gln Gly Asp
        595                 600                 605

Asp Asn Gly Gly Ala Asp Ala Glu Leu Leu Ala Asn Thr Leu Asn Ile
    610                 615                 620

Cys Ala Gly His Asn Glu Asp Ile Leu Ser His Tyr Glu Tyr Thr Ala
625                 630                 635                 640

Leu Ser Ser Leu Thr Asn Lys Ile Cys Gln Arg Leu Ser Gln Ile Gln
                645                 650                 655

Asp Lys Lys Met Leu Glu Ile Glu Glu Gly Ser Ile Lys Asp Lys Glu
            660                 665                 670

Met Glu Leu Glu Ile Gln Thr Leu Val Lys Leu Val Leu Gln Glu Thr
        675                 680                 685

Ser Gly Gly Ile Asp Arg Asn Ile Lys Gln Thr Phe Leu Ser Val Phe
    690                 695                 700

Lys Thr Phe Tyr Tyr Arg Ala Tyr His Asp Ala Lys Thr Ile Asp Ala
705                 710                 715                 720

His Ile Phe Gln Val Leu Phe Glu Pro Val Val
                725                 730
```

<210> SEQ ID NO 7
<211> LENGTH: 2196
<212> TYPE: DNA
<213> ORGANISM: Artificial sequence
<220> FEATURE:
<223> OTHER INFORMATION: Sequence encoding TPS2 of Coleus forskohlii - codon optimized for expression in S. cerevisiae

<400> SEQUENCE: 7

```
atgtccagag ttgcttcctt ggatgctttg aatggtattc aaaaagttgg tccagctacc        60
attggtactc cagaagaaga aaacaagaag atcgaagatt ccatcgaata cgtcaaagaa       120
ttattgaaaa ccatgggtga cggtagaatc tctgtttctc catatgatac tgctatcgtc       180
gccttgatta ggatttggaa aggtggtgat ggtccagaat tccatcttg tttggaatgg        240
attgcccaaa atcaattggc tgatggttct tggggtgatc atttttctg tatctacgat        300
agagttgtta caccgctgc ttgtgttgtt gctttgaaat cttggaatgt tcacgccgat        360
aagattgaaa aggtgccgt ttacttgaaa gaaaacgtcc acaaattgaa ggacggtaag        420
atagaacata tgccagctgg ttttgaattc gttgttccag caactttgga agagctaaa        480
gctttgggta ttaaggggttt gccatatgat gatccattca tcagagaaat ctactccgct       540
aagcaaacta gattgactaa gattccaaag ggtatgatct acgaatctcc aacctctttg       600
```

```
ttgtactctt tggatggttt agaaggtttg aatgggata agatcttgaa gttgcaatca      660
gctgacggtt ctttcatcac ttctgttcct tctactgcct tcgttttcat gcataccaac    720
gatttgaagt gccatgcctt tattaagaac gctttgacta actgtaatgg tggtgttcca    780
catacttacc cagttgatat ttttgctaga ttgtgggccg ttgacagatt gcaaagattg    840
ggtatttcta gattcttcga accagaaatc aaatacttga tggaccacat caacaacgtt    900
tggagagaaa agggtgtttt ctcatccaga cattctcaat tcgccgatat tgatgatacc    960
tccatgggta tcagattatt gaagatgcat ggttacaacg ttaacccaaa cgctttggaa    1020
catttcaagc aaaaggatgg taaattcacc tgttacgccg atcaacatat tgaatctcca    1080
tctccaatgt ataacttgta cagagctgcc caattgagat ttccaggtga agaaatttta    1140
caacaagcct tgcaattcgc ctacaacttc ttgcacgaaa atttggcttc taaccacttc    1200
caagaaaagt gggttatctc cgatcatttg atcgatgaag ttagaatcgg tttgaaaatg    1260
ccatggtatg ctactttgcc aagagttgaa gcttcttact acttgcaaca ttacggtggt    1320
tcttccgatg tttggattgg taaaaccttg tatagaatgc agaaaatctc taacgacacc    1380
tacaagattt tggctcaatt ggatttcaac aagtgccaag ctcaacatca attagaatgg    1440
atgtctatga aggaatggta tcaatccaac aacgtaaaag aattcggtat ctccaagaaa    1500
gaattgttgt tggcttactt tttggctgct gctactatgt tgaacctga aagaactcaa    1560
gaaagaatca tgtgggctaa gacccaagtt gtttctagaa tgattacctc attcttgaac    1620
aaagaaaaca ctatgtcctt cgacttgaag attgctttgt tgactcaacc acaacaccaa    1680
atcaatggtt ccgaaatgaa gaatggtttg gcacaaactt taccagctgc cttcagacaa    1740
ttattgaaag aattcgacaa gtacaccaga caccaattga aaatacttg aacaagtgg     1800
ttgatgaagt tgaagcaagg tgatgataac ggtggtgctg atgctgaatt attggctaac   1860
actttgaaca tttgcgccgg tcataacgaa gatattttgt cccattacga atacaccgcc   1920
ttgtcatctt tgaccaacaa gatttgtcaa agattgtccc aaatccaaga taagaagatg   1980
ttggaaatcg aagaaggttc catcaaggac aaagaaatgg aattggaaat tcaaaccttg   2040
gtcaagttgg tattgcaaga aacttctggt ggtatcgaca gaaacatcaa gcaaactttc   2100
ttgtccgttt tcaagacctt ctactacaga gcttaccatg atgctaagac cattgatgcc   2160
catatcttcc aagttttgtt cgaacctgtt gtttaa                             2196
```

<210> SEQ ID NO 8
<211> LENGTH: 1704
<212> TYPE: DNA
<213> ORGANISM: Artificial sequence
<220> FEATURE:
<223> OTHER INFORMATION: cDNA sequence encoding Coleus forskohlii TPS3

<400> SEQUENCE: 8

```
atgatcacct ctaaatcatc tgcagctgtt aaatgcagcc tcaccacgcc aacagatttg     60
atggggaaaa taaagaggt cttcaacagg gaagtcgata cttctccggc agccatgact    120
actcattcta cagatatacc ctctaatctc tgcataatcg cacccctcca gaggctggga    180
atcgaccaat acttccaatc cgaaatcgac gctgttctac atgatacata caggttatgg    240
caactgaaaa agaaagatat attttcggat attactactc atgcaatggc gttcagactt    300
ttgcgagtca aggatatga agttgcatca gacgaactgg ctccatacgc tgatcaagag    360
cgcattaacc tgcaaaccat tgatgtgccg acagttgttg agctatacag agcagcacag    420
gagagattaa ctgaagaaga tagcactctt gagaaactgt atgtttggac cagcgccttt    480
```

```
ctgaagcagc agttgctcac tgatgccatt cctgacaaga aattgcacaa acaagtggaa    540
tactacttga agaactacca tggcatatta gatagaatgg gagtgagacg aaacctcgac    600
ctatatgaca taagccatta taaaagtctc aaagctgctc acaggttcta taatctgagt    660
aatgaagata tcctagcatt tgcgaggcaa gattttaata ttagccaagc ccaacaccag    720
aaagaacttc agcagctgca aaggtggtat gcagattgta ggttggacac gttgaaattt    780
ggaagagatg tagtgcgtat aggaaatttt ctgacttcag caatgattgg tgatcctgaa    840
ttgtctgacc tccgtctagc gtttgccaaa catatagtgc tcgtaacacg tattgatgat    900
tttttcgatc acggtgggcc taagaagaa tcatacgaga tccttgaatt agtaaaagaa    960
tggaaagaga agccagcagg agaatatgtt tctgaagaag ttgaaatcct atttacagca   1020
gtatacaata cagtaaacga gttggcagaa atggctcata tcgaacaagg acgaagcgtt   1080
aaagaccttc tagttaaact gtgggttgaa atactatcag ttttcagaat agaattggat   1140
acatggacca acgacacagc acttacctta gaagagtact tgtcacaatc ctgggtgtcc   1200
attggctgca gaatctgcat tctccatatca atgcaattcc aaggtgtaaa attatctgat   1260
gaaatgcttc agagtgaaga atgcactgat ttgtgtcggt atgtttcaat ggttgaccgg   1320
ctgctcaacg atgtgcaaac ttttgagaag gaacgcaagg aaaatacagg aaatagtgtg   1380
agccttctgc aagcagctca caaagatgaa agagtcatta tgaagagga agcttgtata   1440 aaggtaaaag aattggctga atataacagg agaaaactga tgcagattgt ctacaaaaca   1500
ggaaccattt tcccaagaaa atgcaaagat ctgttttttga aggcatgcag aattggttgt   1560
tatttgtact caagtggcga cgaatttact tcgcctcaac aaatgatgga agatatgaag   1620
tcactggttt atgaacccct accaatttct cctcctgaag ctaataatgc aagtggagaa   1680
aaaatgagtt gtgtcagcaa ctag                                            1704
```

<210> SEQ ID NO 9
<211> LENGTH: 567
<212> TYPE: PRT
<213> ORGANISM: Coleus forskohlii

<400> SEQUENCE: 9

```
Met Ile Thr Ser Lys Ser Ser Ala Ala Val Lys Cys Ser Leu Thr Thr
 1               5                  10                  15

Pro Thr Asp Leu Met Gly Lys Ile Lys Glu Val Phe Asn Arg Glu Val
            20                  25                  30

Asp Thr Ser Pro Ala Ala Met Thr Thr His Ser Thr Asp Ile Pro Ser
        35                  40                  45

Asn Leu Cys Ile Ile Asp Thr Leu Gln Arg Leu Gly Ile Asp Gln Tyr
    50                  55                  60

Phe Gln Ser Glu Ile Asp Ala Val Leu His Asp Thr Tyr Arg Leu Trp
65                  70                  75                  80

Gln Leu Lys Lys Lys Asp Ile Phe Ser Asp Ile Thr His Ala Met
                85                  90                  95

Ala Phe Arg Leu Leu Arg Val Lys Gly Tyr Glu Val Ala Ser Asp Glu
            100                 105                 110

Leu Ala Pro Tyr Ala Asp Gln Glu Arg Ile Asn Leu Gln Thr Ile Asp
        115                 120                 125

Val Pro Thr Val Val Glu Leu Tyr Arg Ala Ala Gln Glu Arg Leu Thr
    130                 135                 140

Glu Glu Asp Ser Thr Leu Glu Lys Leu Tyr Val Trp Thr Ser Ala Phe
```

```
                145                 150                 155                 160
        Leu Lys Gln Gln Leu Leu Thr Asp Ala Ile Pro Asp Lys Lys Leu His
                        165                 170                 175
        Lys Gln Val Glu Tyr Tyr Leu Lys Asn Tyr His Gly Ile Leu Asp Arg
                        180                 185                 190
        Met Gly Val Arg Arg Asn Leu Asp Leu Tyr Asp Ile Ser His Tyr Lys
                        195                 200                 205
        Ser Leu Lys Ala Ala His Arg Phe Tyr Asn Leu Ser Asn Glu Asp Ile
                210                 215                 220
        Leu Ala Phe Ala Arg Gln Asp Phe Asn Ile Ser Gln Ala Gln His Gln
        225                 230                 235                 240
        Lys Glu Leu Gln Gln Leu Gln Arg Trp Tyr Ala Asp Cys Arg Leu Asp
                        245                 250                 255
        Thr Leu Lys Phe Gly Arg Asp Val Val Arg Ile Gly Asn Phe Leu Thr
                        260                 265                 270
        Ser Ala Met Ile Gly Asp Pro Glu Leu Ser Asp Leu Arg Leu Ala Phe
                275                 280                 285
        Ala Lys His Ile Val Leu Val Thr Arg Ile Asp Asp Phe Phe Asp His
        290                 295                 300
        Gly Gly Pro Lys Glu Glu Ser Tyr Glu Ile Leu Glu Leu Val Lys Glu
        305                 310                 315                 320
        Trp Lys Glu Lys Pro Ala Gly Glu Tyr Val Ser Glu Val Glu Ile
                        325                 330                 335
        Leu Phe Thr Ala Val Tyr Asn Thr Val Asn Glu Leu Ala Glu Met Ala
                        340                 345                 350
        His Ile Glu Gln Gly Arg Ser Val Lys Asp Leu Leu Val Lys Leu Trp
                355                 360                 365
        Val Glu Ile Leu Ser Val Phe Arg Ile Glu Leu Asp Thr Trp Thr Asn
                370                 375                 380
        Asp Thr Ala Leu Thr Leu Glu Glu Tyr Leu Ser Gln Ser Trp Val Ser
        385                 390                 395                 400
        Ile Gly Cys Arg Ile Cys Ile Leu Ile Ser Met Gln Phe Gln Gly Val
                        405                 410                 415
        Lys Leu Ser Asp Glu Met Leu Gln Ser Glu Cys Thr Asp Leu Cys
                        420                 425                 430
        Arg Tyr Val Ser Met Val Asp Arg Leu Leu Asn Asp Val Gln Thr Phe
                435                 440                 445
        Glu Lys Glu Arg Lys Glu Asn Thr Gly Asn Ser Val Ser Leu Leu Gln
        450                 455                 460
        Ala Ala His Lys Asp Glu Arg Val Ile Asn Glu Glu Ala Cys Ile
        465                 470                 475                 480
        Lys Val Lys Glu Leu Ala Glu Tyr Asn Arg Arg Lys Leu Met Gln Ile
                        485                 490                 495
        Val Tyr Lys Thr Gly Thr Ile Phe Pro Arg Lys Cys Lys Asp Leu Phe
                        500                 505                 510
        Leu Lys Ala Cys Arg Ile Gly Cys Tyr Leu Tyr Ser Ser Gly Asp Glu
                        515                 520                 525
        Phe Thr Ser Pro Gln Gln Met Met Glu Asp Met Lys Ser Leu Val Tyr
                530                 535                 540
        Glu Pro Leu Pro Ile Ser Pro Pro Glu Ala Asn Asn Ala Ser Gly Glu
        545                 550                 555                 560
        Lys Met Ser Cys Val Ser Asn
                        565
```

<210> SEQ ID NO 10
<211> LENGTH: 1704
<212> TYPE: DNA
<213> ORGANISM: Artificial sequence
<220> FEATURE:
<223> OTHER INFORMATION: Sequence encoding TPS3 of Coleus forskohlii - codon optimized for expression in S. cerevisiae

<400> SEQUENCE: 10

```
atgatcacct ccaaatcttc cgctgctgtt aagtgttctt tgactactcc aactgatttg      60
atgggtaaga tcaaagaagt tttcaacaga gaagttgata cctctccagc tgctatgact     120
actcattcta ctgatattcc atccaacttg tgcatcatcg ataccttgca aagattgggt     180
atcgaccaat acttccaatc cgaaattgat gctgtcttgc atgatactta cagattgtgg     240
caattgaaga agaaggacat cttctctgat attaccactc atgctatggc cttcagatta     300
ttgagagtta agggttacga agttgcctct gatgaattgg ctccatatgc tgatcaagaa     360
agaatcaact gcaaaccat tgatgttcca accgtcgtcg aattatacag agctgcacaa      420
gaaagattga ccgaagaaga ttctaccttg gaaaagttgt acgtttggac ttctgctttc     480
ttgaagcaac aattattgac cgatgccatc ccagataaga agttgcataa gcaagtcgaa     540
tattacttga gaactacca cggtatcttg atagaatgg gtgttagaag aaacttggac       600
ttgtacgata tctcccacta caaatctttg aaggctgctc atagattcta aacttgtct      660
aacgaagata ttttggcctt cgccagacaa gatttcaaca tttctcaagc ccaacaccaa     720
aaagaattgc aacaattgca agatggtac gccgattgca gattggatac tttgaaattc      780
ggtagagatg tcgtcagaat cggtaacttt ttaacctctg ctatgatcgg tgatccagaa     840
ttgtctgatt tgagattggc ttttgctaag cacatcgttt tggttaccag aatcgatgat     900
ttcttcgatc atggtggtcc aaaagaagaa tcctacgaaa ttttggaatt ggtcaaagaa     960
tggaaagaaa agccagctgg tgaatacgtt tctgaagaag tcgaaatctt attcaccgct    1020
gtttacaaca ccgttaacga attggctgaa atggcccata ttgaacaagg tagatctgtt    1080
aaggatttgt ggttaagtt gtgggtcgaa atattgtccg ttttcagaat cgaattggat    1140
acctggacta acgatactgc tttgactttg gaagaatact tgtcccaatc ctgggtttct    1200
attggttgca gaatctgcat tttgatctcc atgcaattcc aaggtgttaa gttgagtgac    1260
gaaatgttgc aaagtgaaga atgtaccgat ttgtgcagat acgtttccat ggtcgataga    1320
ttattgaacg atgtccaaac cttcgaaaaa gaaagaaaag aaaacaccgg taactccgtt    1380
tctttgttgc aagctgctca aaagacgaa agagttatca cgaagaaga gcctgcatc      1440
aaggtaaaag aattagccga atacaataga agaaagttga tgcaaatcgt ctacaagacc    1500
ggtactattt tcccaagaaa atgcaaggac ttgttcttga aggcttgtag aattggttgc    1560
tacttgtact cttctggtga tgaattcact tcccccacaac aaatgatgga agatatgaag    1620
tccttggtct atgaaccatt gccaatttct ccacctgaag ctaacaatgc atctggtgaa    1680
aaaatgtcct gcgtcagtaa ctga                                          1704
```

<210> SEQ ID NO 11
<211> LENGTH: 587
<212> TYPE: PRT
<213> ORGANISM: Coleus forskohlii

<400> SEQUENCE: 11

Met Ser Ile Thr Ile Asn Leu Arg Val Ile Ala Phe Pro Gly His Gly

-continued

```
 1               5                  10                 15
Val Gln Ser Arg Gln Gly Ile Phe Ala Val Met Glu Phe Pro Arg Asn
             20                 25                 30
Lys Asn Thr Phe Lys Ser Ser Phe Ala Val Lys Cys Ser Leu Ser Thr
             35                 40                 45
Pro Thr Asp Leu Met Gly Lys Ile Lys Glu Lys Leu Ser Glu Lys Val
 50                 55                 60
Asp Asn Ser Val Ala Ala Met Ala Thr Asp Ser Ala Asp Met Pro Thr
 65                 70                 75                 80
Asn Leu Cys Ile Val Asp Ser Leu Gln Arg Leu Gly Val Glu Lys Tyr
                 85                 90                 95
Phe Gln Ser Glu Ile Asp Thr Val Leu Asp Asp Ala Tyr Arg Leu Trp
                100                105                110
Gln Leu Lys Gln Lys Asp Ile Phe Ser Asp Ile Thr Thr His Ala Met
                115                120                125
Ala Phe Arg Leu Leu Arg Val Lys Gly Tyr Asp Val Ser Ser Glu Glu
130                135                140
Leu Ala Pro Tyr Ala Asp Gln Glu Gly Met Asn Leu Gln Thr Ile Asp
145                150                155                160
Leu Ala Ala Val Ile Glu Leu Tyr Arg Ala Ala Gln Glu Arg Val Ala
                165                170                175
Glu Glu Asp Ser Thr Leu Glu Lys Leu Tyr Val Trp Thr Ser Thr Phe
                180                185                190
Leu Lys Gln Gln Leu Leu Ala Gly Ala Ile Pro Asp Gln Lys Leu His
                195                200                205
Lys Gln Val Glu Tyr Tyr Leu Lys Asn Tyr His Gly Ile Leu Asp Arg
210                215                220
Met Gly Val Arg Lys Gly Leu Asp Leu Tyr Asp Ala Gly Tyr Tyr Lys
225                230                235                240
Ala Leu Lys Ala Ala Asp Arg Leu Val Asp Leu Cys Asn Glu Asp Leu
                245                250                255
Leu Ala Phe Ala Arg Gln Asp Phe Asn Ile Asn Gln Ala Gln His Arg
                260                265                270
Lys Glu Leu Glu Gln Leu Gln Arg Trp Tyr Ala Asp Cys Arg Leu Asp
                275                280                285
Lys Leu Glu Phe Gly Arg Asp Val Val Arg Val Ser Asn Phe Leu Thr
                290                295                300
Ser Ala Ile Leu Gly Asp Pro Glu Leu Ser Glu Val Arg Leu Val Phe
305                310                315                320
Ala Lys His Ile Val Leu Val Thr Arg Ile Asp Asp Phe Phe Asp His
                325                330                335
Gly Gly Pro Arg Glu Glu Ser His Lys Ile Leu Glu Leu Ile Lys Glu
                340                345                350
Trp Lys Glu Lys Pro Ala Gly Glu Tyr Val Ser Lys Glu Val Glu Ile
                355                360                365
Leu Tyr Thr Ala Val Tyr Asn Thr Val Asn Glu Leu Ala Glu Arg Ala
                370                375                380
Asn Val Glu Gln Gly Arg Asn Val Glu Pro Phe Leu Arg Thr Leu Trp
385                390                395                400
Val Gln Ile Leu Ser Ile Phe Lys Ile Glu Leu Asp Thr Trp Ser Asp
                405                410                415
Asp Thr Ala Leu Thr Leu Asp Asp Tyr Leu Asn Asn Ser Trp Val Ser
                420                425                430
```

```
Ile Gly Cys Arg Ile Cys Ile Leu Met Ser Met Gln Phe Ile Gly Met
        435                 440                 445

Lys Leu Pro Glu Glu Met Leu Leu Ser Glu Glu Cys Val Asp Leu Cys
    450                 455                 460

Arg His Val Ser Met Val Asp Arg Leu Leu Asn Asp Val Gln Thr Phe
465                 470                 475                 480

Glu Lys Glu Arg Lys Glu Asn Thr Gly Asn Ala Val Ser Leu Leu Leu
                485                 490                 495

Ala Ala His Lys Gly Glu Arg Ala Phe Ser Glu Glu Ala Ile Ala
            500                 505                 510

Lys Ala Lys Tyr Leu Ala Asp Cys Asn Arg Arg Ser Leu Met Gln Ile
        515                 520                 525

Val Tyr Lys Thr Gly Thr Ile Phe Pro Arg Lys Cys Lys Asp Met Phe
    530                 535                 540

Leu Lys Val Cys Arg Ile Gly Cys Tyr Leu Tyr Ala Ser Gly Asp Glu
545                 550                 555                 560

Phe Thr Ser Pro Gln Gln Met Met Glu Asp Met Lys Ser Leu Val Tyr
                565                 570                 575

Glu Pro Leu Gln Ile His Pro Pro Ala Asn
            580                 585

<210> SEQ ID NO 12
<211> LENGTH: 1764
<212> TYPE: DNA
<213> ORGANISM: Coleus forskohlii

<400> SEQUENCE: 12
atgtcaatca ccatcaacct tcgagttatc gctttccccg gccatggagt tcagagcagg      60
caaggaatat ttgcagtcat ggaatttcca aggaacaaga cacctttaa atcatccttt     120
gctgttaaat gcagcctctc tactccaaca gatttgatgg aaagataaa agaaaagttg     180
agcgagaagg ttgataattc tgtggcagcc atggctactg attctgccga tatgcccact     240
aatctctgca tcgtcgactc cctccagagg ctgggagtcg aaaatatttt ccaatccgaa     300
atcgacactg ttctcgatga tgcataccgg ttatggcagc tgaagcagaa agatatattt     360
tcagacatta ctactcatgc aatggcgttt agacttctgc gagtcaaagg atacgatgtt     420
tcatcagagg agctggctcc atacgctgat caagagggca tgaacttgca acgattgat     480
ctggcggcgg tcatcgagct gtacagagca gcacaggaga gagtggctga ggaagacagc     540
actcttgaga aactgtatgt ctggaccagc acctttctga gcagcagtt gctggctggc     600
gccattcctg accagaaatt gcacaaacag gtggagtact acttgaagaa ctaccacggc     660
atattagata gaatgggagt tagaaaagga ctcgacctgt atgatgctgg ctattacaag     720
gccctcaaag ctgcagatag gttggttgat ctatgcaatg aagaccttct agcatttgca     780
aggcaagatt ttaatattaa ccaagcccaa caccgcaaag aacttgagca actgcaaagg     840
tggtatgcag attgtaggtt ggacaaactc gagtttggaa gagatgtggt gcgtgtatcg     900
aattttctga cttcagccat ccttggtgat ccagagcttt ctgaagtccg tctagtgttt     960
gccaaacata ttgtgctagt gactaggata atgattttt cgatcatgg cgggcctaga    1020
gaagaatcac acaagatcct gaactaataa aagaatgga agagaagcc agctggagaa    1080
tatgtttcca agaagttga gatcctatat accgcggtgt acaataggt aaacgagttg    1140
gcagagaggg caaatgttga acaagggcga atgttgaac catttctacg tacactgtgg    1200
```

-continued

```
gttcaaatac tgtcgatttt caagatagag ttggatacat ggagcgatga cacagcacta   1260
accttggatg attacttgaa caactcatgg gtgtcgattg gttgtagaat ctgcattctc   1320
atgtccatgc aattcattgg tatgaagtta ccagaagaaa tgcttctcag tgaagagtgc   1380
gttgatttgt gtaggcatgt ttccatggtc gaccgtctgc tcaatgatgt ccaaactttt   1440
gagaaggaac ggaaagaaaa tacaggaaac gctgtgagcc ttctgctagc agctcacaag   1500
ggtgaaagag ccttcagtga agaggaagcc atagcaaaag cgaaatattt ggctgactgt   1560
aacaggagaa gtctgatgca gattgtgtat aaaacaggaa ccattttccc aagaaaatgc   1620
aaagatatgt tcttgaaggt gtgcaggatt ggttgctatt tgtatgcgag tggcgacgaa   1680
tttacttccc ctcaacaaat gatggaagat atgaagtcat tagtttatga gcccctccaa   1740
attcaccctc cacctgctaa ctaa                                           1764
```

METHODS AND MATERIALS FOR BIOSYNTHESIS OF MANOYL OXIDE

This application is a U.S. national phase of International Application No. PCT/EP2015/076595, filed on Nov. 13, 2015, which claims the benefit of DK Application No.: PA201470694, filed Nov. 13, 2014. The entire disclosure contents of these applications are herewith incorporated by reference in their entirety into the present application.

BACKGROUND OF THE INVENTION

Field of Invention

This disclosure relates recombinant production of manoyl oxide in recombinant hosts. The disclosure also provides methods for producing terpenoids using manoyl oxide as a precursor or an intermediate.

Description of Related Art

Terpenoids are a diverse class of molecules with a wide variety of applications, including pharmaceuticals, cosmetics, food preparation, and fragrances. One such terpenoid, forskolin, is produced by *Coleus forskohlii* (*C. forskohlii*). Forskolin has been shown to decrease intraocular pressure and is used as an antiglaucoma agent (Wagh et al., 2012, J Postgrad Med. 58(3):199-202). Moreover, a water-soluble analogue of forskolin (NKH477) has been approved for commercial use in Japan for treatment of acute heart failure and heart surgery complications (Kikura et al., 2004, Pharmacol Res. 49(3):275-81). Forskolin also acts as bronchodilator (Yousif & Thulesius, 1999, J Pharm Pharmacol. 51(2):181-6) and may be used to treat obesity by contributing to higher rates of body fat burning and promoting lean body mass formation (Godard et al., Obes Res. 2005, 13(8):1335-43). Another terpenoid, ambrox, is a component of ambergris, a substance secreted from the intestines of the sperm whale, is useful in the perfume industry (Schalk et al., J Am Chem Soc. 134(46):18900-3).

The diterpene, manoyl oxide, is a precursor of forskolin and ambrox. Pateraki et al., 2014, Plant Physiol. 164(3): 1222-6 showed that manoyl oxide localizes to oil bodies in *C. forskohlii*. Pateraki also demonstrated functional characterization of four CfTPSs from *C. forskohlii*. CfTPS2 was found to synthesize the intermediate copal-8-ol diphosphate, and in combination with CfTPS3 or CfTPS4 resulted in the stereospecific formation of (13R) manoyl oxide in planta.

As recovery and purification of forskolin and ambrox have proven to be labor intensive and inefficient (see, e.g., Nielsen et al., 2014, Appl Environ Microbiol. 80(23):7258-65, Harde & Singhal, 2012, Separation and Purification Technology 96:20-5 and Frija et al., 2011, 111(8):4418-52), there remains a need for a recombinant production system that can produce high yields of desired forskolin and ambrox, as well as their precursors, including manoyl oxide.

SUMMARY OF INVENTION

It is against the above background that the present invention provides certain advantages and advancements over the prior art.

Although this invention disclosed herein is not limited to specific advantages or functionalities, the invention provides a recombinant host comprising:
(a) a gene encoding a geranylgeranyl diphosphate synthase (GGPPS) polypeptide;
(b) a gene encoding a polypeptide capable of catalyzing formation of copal-8-ol diphosphate from geranylgeranyl diphosphate (GGPP); and
(c) a gene encoding a polypeptide capable of catalyzing formation of manoyl oxide from copal-8-ol diphosphate;
wherein at least one of the genes is a heterologous gene; and
wherein the recombinant host is capable of producing manoyl oxide.

In some aspects of the recombinant host disclosed herein, the GGPPS polypeptide comprises a GGPPS7 polypeptide having at least 70% identity to the amino acid sequence set forth in SEQ ID NO:2 or a GGPPS10 polypeptide having at least 70% identity to the amino acid sequence set forth in SEQ ID NO:2.

In some aspects of the recombinant host disclosed herein, the enzyme capable of catalyzing formation of copal-8-ol diphosphate from GGPP is a terpene synthase 2 (TPS2) polypeptide.

In some aspects of the recombinant host disclosed herein, the enzyme capable of catalyzing formation of manoyl oxide from copal-8-ol diphosphate is a terpene synthase 3 (TPS3) polypeptide or a terpene synthase 4 (TPS4) polypeptide.

In some aspects of the recombinant host disclosed herein, the TPS3 polypeptide comprises a TPS3 polypeptide having at least 70% identity to an amino acid sequence set forth in SEQ ID NO:9.

In some aspects of the recombinant host disclosed herein, the TPS4 polypeptide comprises a TPS4 polypeptide having at least 70% identity to an amino acid sequence set forth in SEQ ID NO:11.

In some aspects of the recombinant host disclosed herein, the recombinant host comprises a plant cell, a mammalian cell, an insect cell, a fungal cell, or a bacterial cell.

In some aspects of the recombinant host disclosed herein, the bacterial cell comprises *Escherichia* bacteria cells, *Lactobacillus* bacteria cells, *Lactococcus* bacteria cells, *Cornebacterium* bacteria cells, *Acetobacter* bacteria cells, *Acinetobacter* bacteria cells, or *Pseudomonas* bacterial cells.

In some aspects of the recombinant host disclosed herein, the fungal cell comprises a yeast cell.

In some aspects of the recombinant host disclosed herein, the yeast cell is a cell from *Saccharomyces cerevisiae, Schizosaccharomyces pombe, Yarrowia lipolytica, Candida glabrata, Ashbya gossypii, Cyberlindnera jadinii, Pichia pastoris, Kluyveromyces lactis, Hansenula polymorpha, Candida boidinii, Arxula adeninivorans, Xanthophyllomyces dendrorhous,* or *Candida albicans* species.

In some aspects of the recombinant host disclosed herein, the yeast cell is a *Saccharomycete*.

In some aspects of the recombinant host disclosed herein, the yeast cell is a cell from the *Saccharomyces cerevisiae* species.

The invention also provides a method of producing manoyl oxide, comprising:
(a) growing the recombinant host disclosed herein in a culture medium, under conditions in which any of the genes disclosed herein are expressed;
wherein the manoyl oxide is synthesized by said host; and/or
(b) optionally quantifying the manoyl oxide; and/or
(c) optionally isolating the manoyl oxide.

In some aspects of the method disclosed herein, the manoyl oxide is (13R) manoyl oxide.

The invention also provides a method for producing a terpenoid, comprising:

(a) growing the recombinant host disclosed herein in a culture medium, under conditions in which any of the genes disclosed herein are expressed;
    wherein the manoyl oxide is synthesized by said host;
(b) isolating the manoyl oxide produced by said host; and/or
(c) converting the manoyl oxide into a terpenoid.

In some aspects of the method disclosed herein, the manoyl oxide is isolated from the microorganism and/or from the cultivation medium.

In some aspects of the method disclosed herein, the manoyl oxide is converted to the terpenoid by organic chemical synthesis.

In some aspects of the method disclosed herein, the terpenoid is forskolin.

In some aspects of the method disclosed herein, the terpenoid is ambrox.

These and other features and advantages of the present invention will be more fully understood from the following detailed description taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present invention can be best understood when read in conjunction with the following drawings, where like structure is indicated with like reference numerals and in which.

DETAILED DESCRIPTION OF THE INVENTION

Figure 1:
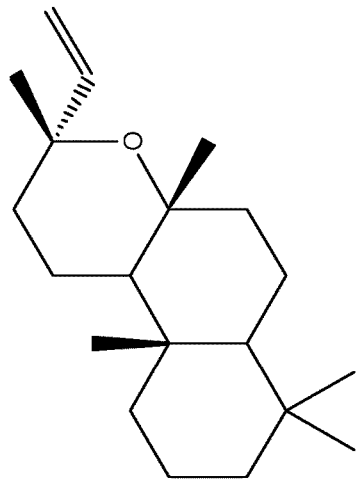
FIG. 1 shows the structures of manoyl oxide, (13R) manoyl oxide, forskolin, and ambrox.
Figure 1:
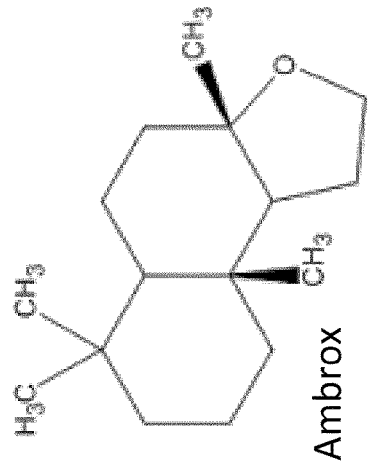
Figure 1:
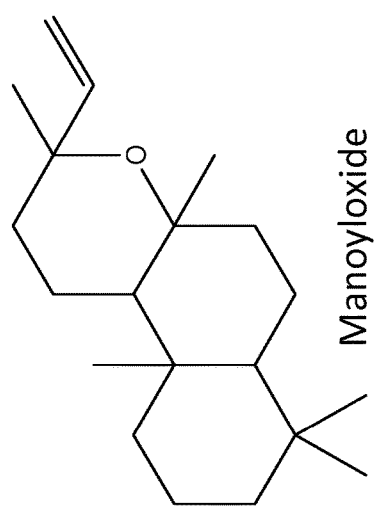
Figure 1:
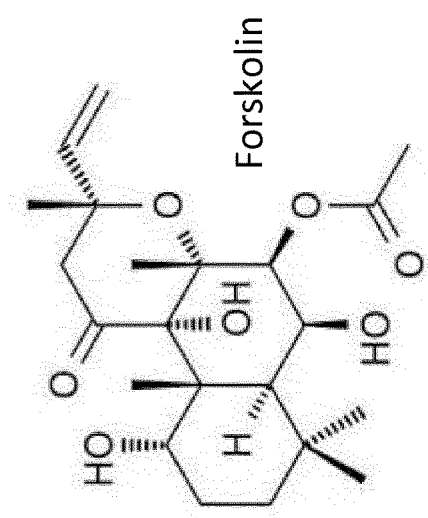

Before describing the present invention in detail, a number of terms will be defined. As used herein, the singular forms "a," "an," and "the" include plural referents unless the context clearly dictates otherwise. For example, reference to a "nucleic acid" means one or more nucleic acids.

It is noted that terms like "preferably," "commonly," and "typically" are not utilized herein to limit the scope of the claimed invention or to imply that certain features are critical, essential, or even important to the structure or function of the claimed invention. Rather, these terms are merely intended to highlight alternative or additional features that can or cannot be utilized in a particular embodiment of the present invention.

For the purposes of describing and defining the present invention it is noted that the term "substantially" is utilized herein to represent the inherent degree of uncertainty that can be attributed to any quantitative comparison, value, measurement, or other representation. The term "substantially" is also utilized herein to represent the degree by which a quantitative representation can vary from a stated reference without resulting in a change in the basic function of the subject matter at issue.

Methods well known to those skilled in the art can be used to construct genetic expression constructs and recombinant cells according to this invention. These methods include in vitro recombinant DNA techniques, synthetic techniques, in vivo recombination techniques, and polymerase chain reaction (PCR) techniques. See, for example, techniques as described in Green & Sambrook, 2012, MOLECULAR CLONING: A LABORATORY MANUAL, Fourth Edition, Cold Spring Harbor Laboratory, New York; Ausubel et al., 1989, CURRENT PROTOCOLS IN MOLECULAR BIOLOGY, Greene Publishing Associates and Wiley Interscience, New York, and PCR Protocols: A Guide to Methods and Applications (Innis et al., 1990, Academic Press, San Diego, Calif.).

As used herein, the terms "polynucleotide," "nucleotide," "oligonucleotide," and "nucleic acid" can be used interchangeably to refer to nucleic acid comprising DNA, RNA, derivatives thereof, or combinations thereof.

As used herein, the terms "microorganism," "microorganism host," "microorganism host cell," "recombinant host," and "recombinant host cell" can be used interchangeably. As used herein, the term "recombinant host" is intended to refer to a host, the genome of which has been augmented by at least one DNA sequence. Such DNA sequences include but are not limited to genes that are not naturally present, DNA sequences that are not normally transcribed into RNA or translated into a protein ("expressed"), and other genes or DNA sequences which one desires to introduce into a host. It will be appreciated that typically the genome of a recombinant host described herein is augmented through stable introduction of one or more recombinant genes. Generally, introduced DNA is not originally resident in the host that is the recipient of the DNA, but it is within the scope of this disclosure to isolate a DNA segment from a given host, and to subsequently introduce one or more additional copies of that DNA into the same host, e.g., to enhance production of the product of a gene or alter the expression pattern of a gene. In some instances, the introduced DNA will modify or even replace an endogenous gene or DNA sequence by, e.g., homologous recombination or site-directed mutagenesis. Suitable recombinant hosts include microorganisms.

As used herein, the term "recombinant gene" refers to a gene or DNA sequence that is introduced into a recipient host, regardless of whether the same or a similar gene or DNA sequence may already be present in such a host. "Introduced," or "augmented" in this context, is known in the art to mean introduced or augmented by the hand of man. Thus, a recombinant gene can be a DNA sequence from another species or can be a DNA sequence that originated from or is present in the same species but has been incorporated into a host by recombinant methods to form a recombinant host. It will be appreciated that a recombinant gene that is introduced into a host can be identical to a DNA sequence that is normally present in the host being transformed, and is introduced to provide one or more additional copies of the DNA to thereby permit overexpression or modified expression of the gene product of that DNA. In some aspects, said recombinant genes are encoded by cDNA. In other embodiments, recombinant genes are synthetic and/or codon-optimized for expression in *S. cerevisiae*.

As used herein, the term "engineered biosynthetic pathway" refers to a biosynthetic pathway that occurs in a recombinant host, as described herein. In some aspects, one or more steps of the biosynthetic pathway do not naturally occur in an unmodified host. In some embodiments, a heterologous version of a gene is introduced into a host that comprises an endogenous version of the gene.

As used herein, the term "endogenous" gene refers to a gene that originates from and is produced or synthesized within a particular organism, tissue, or cell. In some embodiments, the endogenous gene is a yeast gene. In some embodiments, the gene is endogenous to *S. cerevisiae*, including, but not limited to *S. cerevisiae* strains. In some embodiments, an endogenous yeast gene is overexpressed. As used herein, the term "overexpress" is used to refer to the expression of a gene in an organism at levels higher than the level of gene expression in a wild type organism. See, e.g., Prelich, 2012, *Genetics* 190:841-54. In some embodiments, an endogenous yeast gene is deleted. See, e.g., Giaever & Nislow, 2014, *Genetics* 197(2):451-65. As used herein, the terms "deletion," "deleted," "knockout," and "knocked out" can be used interchangeably to refer to an endogenous gene that has been manipulated to no longer be expressed in an organism, including, but not limited to, *S. cerevisiae*.

As used herein, the terms "heterologous sequence" and "heterologous coding sequence" are used to describe a sequence derived from a species other than the recombinant host. In some embodiments, the recombinant host is an *S. cerevisiae* cell, and a heterologous sequence is derived from an organism other than *S. cerevisiae*. A heterologous coding sequence, for example, can be from a prokaryotic microorganism, a eukaryotic microorganism, a plant, an animal, an insect, or a fungus different than the recombinant host expressing the heterologous sequence. In some embodiments, a coding sequence is a sequence that is native to the host.

A "selectable marker" can be one of any number of genes that complement host cell auxotrophy, provide antibiotic resistance, or result in a color change. Linearized DNA fragments of the gene replacement vector then are introduced into the cells using methods well known in the art (see below). Integration of the linear fragments into the genome and the disruption of the gene can be determined based on the selection marker and can be verified by, for example, PCR or Southern blot analysis. Subsequent to its use in selection, a selectable marker can be removed from the genome of the host cell by, e.g., Cre-LoxP systems (see, e.g., Gossen et al., 2002, *Ann. Rev. Genetics* 36:153-173 and U.S. 2006/0014264). Alternatively, a gene replacement vector can be constructed in such a way as to include a portion of the gene to be disrupted, where the portion is devoid of any endogenous gene promoter sequence and encodes none, or an inactive fragment of, the coding sequence of the gene.

As used herein, the terms "variant" and "mutant" are used to describe a protein sequence that has been modified at one or more amino acids, compared to the wild-type sequence of a particular protein.

The structures of manoyl oxide and (13R) manoyl oxide (13R-MO) are shown in FIG. 1. As used herein, the term "terpenoid" refers any terpenoid that can be produced using manoyl oxide as a precursor or an intermediate during synthesis. In some embodiments, the terpenoid is a diterpenoid. Non-limiting examples of terpenoids include forskolin and ambrox, the structures of which are also shown in FIG.

1. As described herein, manoyl oxide can be produced in vivo, in vitro, or by bioconversion.

As used herein, the term "substituted manoyl oxide" refers to a manoyl oxide molecule, wherein one or more hydrogens have been substituted with another moiety, also referred to as a "substituent." Non-limiting examples of substituents include hydroxyl, oxo, carboxyl, carbonyl, or acyl groups. In some embodiments, the substituted manoyl oxide is forskolin.

In some embodiments, manoyl oxide is produced in vivo through expression of one or more enzymes involved in the manoyl oxide biosynthetic pathway in a recombinant host. For example, a geranylgeranyl diphosphate (GGPP)-producing recombinant host expressing a gene encoding a polypeptide capable of catalyzing conversion of GGPP to copal-8-ol diphosphate and a gene encoding a polypeptide capable of catalyzing conversion of copal-8-ol diphosphate to manoyl oxide can produce manoyl oxide in vivo.

In some embodiments, a host comprises i) a heterologous nucleic acid encoding a geranylgeranyl diphosphate synthase (GGPPS), ii) a heterologous nucleic acid encoding an enzyme capable of catalyzing formation of copal-8-ol diphosphate from geranylgeranyl diphosphate (GGPP), and iii) a heterologous nucleic acid encoding an enzyme capable of catalyzing formation of manoyl oxide from copal-8-ol diphosphate.

The GGPPS is capable of catalyzing conversion of farnesyl diphosphate (FPP) and isopentenyl diphosphate (IPP) to GGPP. In particular, the GGPPS can be any enzyme classified under EC 2.5.1.29. A host may comprise an endogenous GGPPS. In some embodiments, a manoyl oxide-producing host comprising a heterologous GGPPS produces higher amounts of manoyl oxide than a manoyl oxide-producing host comprising an endogenous GGPPS.

In some embodiments, the GGPPS is derived from *Synechococcus* sp., such as GGPPS7 of SEQ ID NO:2 or a GGPPS having at least 70% identity to SEQ ID NO:2. The GGPPS7 having an amino acid sequence set forth in SEQ ID NO:2 can be encoded by a nucleotide sequence set forth in SEQ ID NO:1. In other embodiments, the GGPPS is derived from *Aspergillus nidulans*, such as GGPPS10 of SEQ ID NO:4 or a GGPPS having at least 70% identity to SEQ ID NO:4. The GGPPS10 having an amino acid sequence set forth in SEQ ID NO:4 can be encoded by a nucleotide sequence set forth in SEQ ID NO:3. In some embodiments, a GGPPS polypeptide is encoded by a nucleotide sequence having at least 70% identity to SEQ ID NO:1 or SEQ ID NO:3.

Figure 2A:
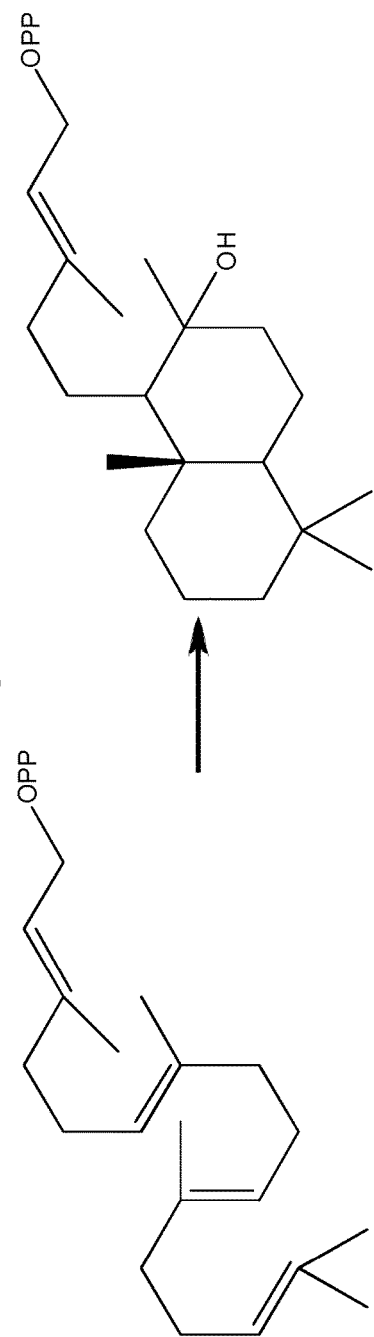
FIG. 2A shows the reaction catalyzed by a terpene synthase 2 (TPS2) polypeptide.

In some embodiments, the enzyme capable of catalyzing formation of copal-8-ol diphosphate from GGPP comprises a terpene synthase 2 (TPS2) enzyme. The reaction catalysed by TPS2 is shown in FIG. 2A. In some embodiments, the TPS2 is TPS2 from *C. forskohlii*. In particular, the TPS2 can be the TPS2 of SEQ ID NO:6 or a TPS2 having at least 70% identity to SEQ ID NO:6. The TPS2 having an amino acid sequence set forth in SEQ ID NO:6 can be encoded by a nucleotide sequence set forth in SEQ ID NO:5 or SEQ ID NO:7. In some embodiments, a TPS2 polypeptide is encoded by a nucleotide sequence having at least 70% identity to SEQ ID NO:5 or SEQ ID NO:7.

Figure 2B:
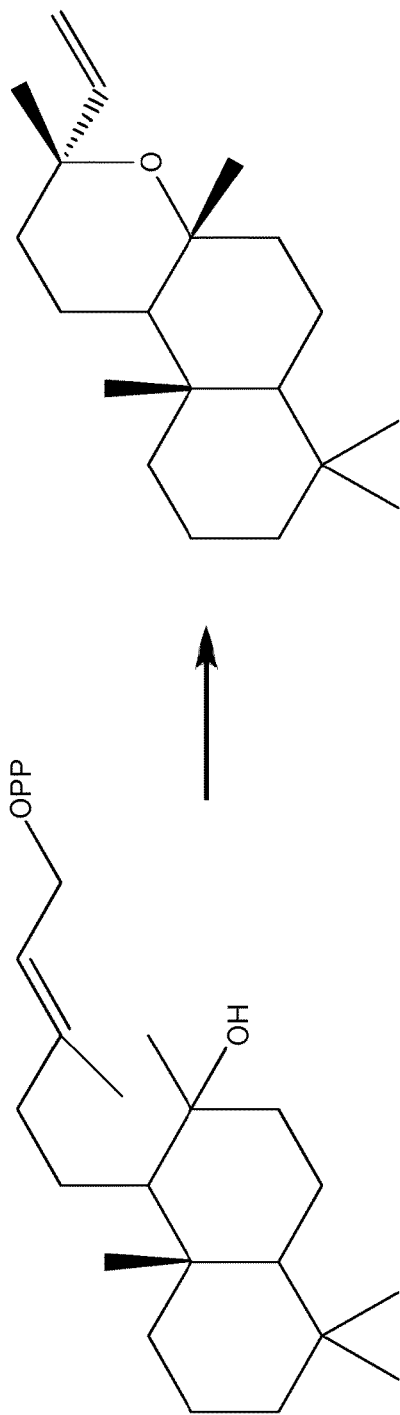
FIG. 2B shows the reaction catalyzed by a terpene synthase 3 (TPS3) or terpene synthase 4 (TPS4) polypeptide.

In some embodiments, the enzyme capable of catalyzing formation of manoyl oxide from copal-8-ol diphosphate comprises a terpene synthase 3 (TPS3) or terpene synthase 4 (TPS4) enzymes. The reaction catalyzed by TPS3 or TPS4 is shown in FIG. 2B. In some embodiments, the TPS3 is a TPS3 from *C. forskohlii*. In particular, the TPS3 can be a TPS3 of SEQ ID NO:9 or a TPS3 having at least 70% identity to SEQ ID NO:9. The TPS3 having an amino acid sequence set forth in SEQ ID NO:9 can be encoded by a nucleotide sequence set forth in SEQ ID NO:8 or SEQ ID NO:10. In some embodiments, a TPS3 polypeptide is encoded by a nucleotide sequence having at least 70% identity to SEQ ID NO:8 or SEQ ID NO:10.

In some embodiments, the TPS4 is a TPS4 from *C. forskohlii*. In particular, the TPS4 can be a TPS4 of SEQ ID NO:11 or a TPS4 having at least 70% identity to SEQ ID NO:11. The TPS4 having an amino acid sequence can be encoded by a nucleotide sequence set forth in SEQ ID NO:12. In some embodiments, a TPS4 polypeptide is encoded by a nucleotide sequence having at least 70% identity to SEQ ID NO:12.

The recombinant hosts described herein are particularly useful for producing manoyl oxide. In some embodiments, the recombinant microorganisms according to the invention are capable of producing at least 2×, preferably at least 10×, more preferably at least 20×, such as at least 50×, for example at least 100× more manoyl oxide, compared to a manoyl oxide-producing organism that does not comprises a heterologous GGPPS, a heterologous TPS2, and/or a heterologous TPS3 or TPS4.

In some embodiments, the recombinant host described herein is capable of producing at least 3 g/L, such as at least 5 g/L, for example at least 7 g/L manoyl oxide after cultivation for approximately 120 h.

In some embodiments, a recombinant host described herein can further comprise i) a heterologous nucleic acid encoding enzymes involved in the biosynthesis of GGPP and/or of farnesyl diphosphate (FPP) and/or ii) a heterologous nucleic acid encoding enzymes involved in the biosynthesis of terpenoids. In some embodiments, a recombinant host is modified to reduce the activity of reactions consuming GGPP for other purposes. Thus, the recombinant host may further contain a construct to silence the expression of non-manoyl oxide pathways consuming GGPP or FPP, thereby providing increased flux towards manoyl oxide or manoyl oxide-derived products. For example, flux to sterol production pathways such as ergosterol may be reduced by downregulation of the ERG9 gene. In a non-limiting example, the native promoter of the ERG9 gene can be substituted for a weaker promoter, which results in lowered expression of ERG9. See, e.g., Asadollahi et al., 2010, Biotechnol Bioeng. 106(1):86-96 and Kennedy & Bard, 2001, Biochim Biophys Acta. 1517(2):177-89.

In another embodiment, a recombinant host described herein can comprise one or more genes encoding one or more enzymes in the MEP pathway or the mevalonate pathway. Such genes can increase the flux of carbon into the diterpene biosynthesis pathway, producing GGPP from IPP and dimethylallyl diphosphate (DMAPP) generated by the pathway.

In addition, expression of a truncated form of the enzyme 3-hydroxy-3-methylglutaryl-CoA reductase (tHMG1) can also increase levels of GGPP. A useful truncated form of yeast HMG reductase (tHMG1) is described in Donald et al., 1997, Appl. Environ. Microbiol. 63, 3341-3344.

In some embodiments, manoyl oxide is produced through contact of a manoyl oxide precursor with one or more enzymes involved in the manoyl oxide pathway in vitro. For example, contacting copal-8-ol diphosphate with a TPS3 or TPS4 polypeptide can result in production of a manoyl oxide in vitro.

In some embodiments, manoyl oxide is produced by whole cell bioconversion. For whole cell bioconversion to occur, a host cell expressing one or more enzymes involved in the manoyl oxide pathway takes up and modifies a manoyl oxide precursor in the cell; following modification in vivo, manoyl oxide remains in the cell and/or is excreted into the culture medium. For example, a host cell expressing a gene encoding a TPS3 or TPS4 polypeptide can take up copal-8-ol diphosphate and modify copal-8-ol diphosphate in the cell; following modification in vivo, manoyl oxide can be excreted into the culture medium. In some embodiments, the cell is permeabilized to take up a substrate to be modified or to excrete a modified product.

In some aspects, manoyl oxide produced herein can be converted to ambrox using a method described by Cambie et al., 1971, *Australian Journal of Chemistry* 24(3):583-91. In other aspects, manoyl oxide produced herein can be converted to forskolin. See, e.g., Nielsen et al., 2014, Appl Environ Microbiol. 80(23):7258-65 and Pateraki et al., 2014, Plant Physiol. 164(3):1222-6.

Functional Homologs

Functional homologs of the polypeptides described above are also suitable for use in producing manoyl oxide in a recombinant host. A functional homolog is a polypeptide that has sequence similarity to a reference polypeptide, and that carries out one or more of the biochemical or physiological function(s) of the reference polypeptide. A functional homolog and the reference polypeptide can be a natural occurring polypeptide, and the sequence similarity can be due to convergent or divergent evolutionary events. As such, functional homologs are sometimes designated in the literature as homologs, or orthologs, or paralogs. Variants of a naturally occurring functional homolog, such as polypeptides encoded by mutants of a wild type coding sequence, can themselves be functional homologs. Functional homologs can also be created via site-directed mutagenesis of the coding sequence for a polypeptide, or by combining domains from the coding sequences for different naturally-occurring polypeptides ("domain swapping"). Techniques for modifying genes encoding functional polypeptides described herein are known and include, inter alia, directed evolution techniques, site-directed mutagenesis techniques and random mutagenesis techniques, and can be useful to increase specific activity of a polypeptide, alter substrate specificity, alter expression levels, alter subcellular location, or modify polypeptide-polypeptide interactions in a desired manner. Such modified polypeptides are considered functional homologs. The term "functional homolog" is sometimes applied to the nucleic acid that encodes a functionally homologous polypeptide.

Functional homologs can be identified by analysis of nucleotide and polypeptide sequence alignments. For example, performing a query on a database of nucleotide or polypeptide sequences can identify homologs of manoyl oxide biosynthesis polypeptides. Sequence analysis can involve BLAST, Reciprocal BLAST, or PSI-BLAST analysis of non-redundant databases using a GGPPS, TPS2, TPS3, or TPS4 amino acid sequence as the reference sequence. Amino acid sequence is, in some instances, deduced from the nucleotide sequence. Those polypeptides in the database that have greater than 40% sequence identity are candidates for further evaluation for suitability as a manoyl oxide biosynthesis polypeptide. Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have domains present in manoyl oxide biosynthesis polypeptides, e.g., conserved functional domains. In some embodiments, nucleic acids and polypeptides are identified from transcriptome data based on expression levels rather than by using BLAST analysis.

Conserved regions can be identified by locating a region within the primary amino acid sequence of a manoyl oxide biosynthesis polypeptide that is a repeated sequence, forms some secondary structure (e.g., helices and beta sheets), establishes positively or negatively charged domains, or represents a protein motif or domain. See, e.g., the Pfam web site describing consensus sequences for a variety of protein motifs and domains on the World Wide Web at sanger.ac.uk/Software/Pfam/ and pfam.janelia.org/. The information included at the Pfam database is described in Sonnhammer et al., *Nucl. Acids Res.*, 26:320-322 (1998); Sonnhammer et al., Proteins, 28:405-420 (1997); and Bateman et al., *Nucl. Acids Res.*, 27:260-262 (1999). Conserved regions also can be determined by aligning sequences of the same or related polypeptides from closely related species. Closely related species preferably are from the same family. In some embodiments, alignment of sequences from two different species is adequate to identify such homologs.

Typically, polypeptides that exhibit at least about 40% amino acid sequence identity are useful to identify conserved regions. Conserved regions of related polypeptides exhibit at least 45% amino acid sequence identity (e.g., at least 50%, at least 60%, at least 70%, at least 80%, or at least 90% amino acid sequence identity). In some embodiments, a conserved region exhibits at least 92%, 94%, 96%, 98%, or 99% amino acid sequence identity.

For example, polypeptides suitable for producing manoyl oxide in a recombinant host include functional homologs of GGPPS, TPS2, TPS3, or TPS4. Methods to modify the substrate specificity of, for example, GGPPS, TPS2, TPS3, or TPS4, are known to those skilled in the art, and include without limitation site-directed/rational mutagenesis approaches, random directed evolution approaches and combinations in which random mutagenesis/saturation techniques are performed near the active site of the enzyme. For example see Osmani et al., 2009, *Phytochemistry* 70: 325-347.

A candidate sequence typically has a length that is from 80% to 200% of the length of the reference sequence, e.g., 82, 85, 87, 89, 90, 93, 95, 97, 99, 100, 105, 110, 115, 120, 130, 140, 150, 160, 170, 180, 190, or 200% of the length of the reference sequence. A functional homolog polypeptide typically has a length that is from 95% to 105% of the length of the reference sequence, e.g., 90, 93, 95, 97, 99, 100, 105, 110, 115, or 120% of the length of the reference sequence, or any range between. A % identity for any candidate nucleic acid or polypeptide relative to a reference nucleic acid or polypeptide can be determined as follows. A reference sequence (e.g., a nucleic acid sequence or an amino acid sequence described herein) is aligned to one or more candidate sequences using the computer program ClustalW (version 1.83, default parameters), which allows alignments of nucleic acid or polypeptide sequences to be carried out across their entire length (global alignment). Chenna et al., 2003, *Nucleic Acids Res.* 31(13):3497-500.

ClustalW calculates the best match between a reference and one or more candidate sequences, and aligns them so that identities, similarities and differences can be determined. Gaps of one or more residues can be inserted into a reference sequence, a candidate sequence, or both, to maximize sequence alignments. For fast pairwise alignment of nucleic acid sequences, the following default parameters are used: word size: 2; window size: 4; scoring method: % age; number of top diagonals: 4; and gap penalty: 5. For multiple alignment of nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method: % age; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The ClustalW output is a sequence alignment that reflects the relationship between sequences. ClustalW can be run, for example, at the Baylor College of Medicine Search Launcher site on the World Wide Web (searchlauncher.bcm.tmc.edu/multi-align/multi-align.html) and at the European Bioinformatics Institute site on the World Wide Web (ebi.ac.uk/clustalw).

To determine % identity of a candidate nucleic acid or amino acid sequence to a reference sequence, the sequences are aligned using ClustalW, the number of identical matches in the alignment is divided by the length of the reference sequence, and the result is multiplied by 100. It is noted that the % identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

It will be appreciated that functional GGPPS, TPS2, TPS3, or TPS4 proteins can include additional amino acids that are not involved in the enzymatic activities carried out by the enzymes. In some embodiments, GGPPS, TPS2, TPS3, or TPS4 are fusion proteins. The terms "chimera," "fusion polypeptide," "fusion protein," "fusion enzyme," "fusion construct," "chimeric protein," "chimeric polypeptide," "chimeric construct," and "chimeric enzyme" can be used interchangeably herein to refer to proteins engineered through the joining of two or more genes that code for different proteins. In some embodiments, a nucleic acid sequence encoding a GGPPS, TPS2, TPS3, or TPS4 polypeptide can include a tag sequence that encodes a "tag" designed to facilitate subsequent manipulation (e.g., to facilitate purification or detection), secretion, or localization of the encoded polypeptide. Tag sequences can be inserted in the nucleic acid sequence encoding the polypeptide such that the encoded tag is located at either the carboxyl or amino terminus of the polypeptide. Non-limiting examples of encoded tags include green fluorescent protein (GFP), human influenza hemagglutinin (HA), glutathione S transferase (GST), polyhistidine-tag (HIS tag), and FIag™ tag (Kodak, New Haven, Conn.). Other examples of tags include a chloroplast transit peptide, a mitochondrial transit peptide, an amyloplast peptide, signal peptide, or a secretion tag.

In some embodiments, a fusion protein is a protein altered by domain swapping. As used herein, the term "domain swapping" is used to describe the process of replacing a domain of a first protein with a domain of a second protein. In some embodiments, the domain of the first protein and the domain of the second protein are functionally identical or functionally similar. In some embodiments, the structure and/or sequence of the domain of the second protein differs from the structure and/or sequence of the domain of the first protein. In some embodiments, a GGPPS, TPS2, TPS3, or TPS4 polypeptide is altered by domain swapping.

Manoyl Oxide Biosynthesis Nucleic Acids

A recombinant gene encoding a polypeptide described herein comprises the coding sequence for that polypeptide, operably linked in sense orientation to one or more regulatory regions suitable for expressing the polypeptide. Because many microorganisms are capable of expressing multiple gene products from a polycistronic mRNA, multiple polypeptides can be expressed under the control of a single regulatory region for those microorganisms, if desired. A coding sequence and a regulatory region are considered to be operably linked when the regulatory region and coding sequence are positioned so that the regulatory region is effective for regulating transcription or translation of the sequence. Typically, the translation initiation site of the translational reading frame of the coding sequence is positioned between one and about fifty nucleotides downstream of the regulatory region for a monocistronic gene.

In many cases, the coding sequence for a polypeptide described herein is identified in a species other than the recombinant host, i.e., is a heterologous nucleic acid. Thus, if the recombinant host is a microorganism, the coding sequence can be from other prokaryotic or eukaryotic microorganisms, from plants or from animals. In some case, however, the coding sequence is a sequence that is native to the host and is being reintroduced into that organism. A native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found. "Regulatory region" refers to a nucleic acid having nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof. A regulatory region typically comprises at least a core (basal) promoter. A regulatory region also may include at least one control element, such as an enhancer sequence, an upstream element or an upstream activation region (UAR). A regulatory region is operably linked to a coding sequence by positioning the regulatory region and the coding sequence so that the regulatory region is effective for regulating transcription or translation of the sequence. For example, to operably link a coding sequence and a promoter sequence, the translation initiation site of the translational reading frame of the coding sequence is typically positioned between one and about fifty nucleotides downstream of the promoter. A regulatory region can, however, be positioned as much as about 5,000 nucleotides upstream of the translation initiation site, or about 2,000 nucleotides upstream of the transcription start site.

The choice of regulatory regions to be included depends upon several factors, including, but not limited to, efficiency, selectability, inducibility, desired expression level, and preferential expression during certain culture stages. It is a routine matter for one of skill in the art to modulate the expression of a coding sequence by appropriately selecting and positioning regulatory regions relative to the coding sequence. It will be understood that more than one regulatory region may be present, e.g., introns, enhancers, upstream activation regions, transcription terminators, and inducible elements.

One or more genes can be combined in a recombinant nucleic acid construct in "modules" useful for a discrete aspect of manoyl oxide production. Combining a plurality of genes in a module, particularly a polycistronic module, facilitates the use of the module in a variety of species. For example, a manoyl oxide biosynthesis gene cluster can be combined in a polycistronic module such that, after insertion of a suitable regulatory region, the module can be introduced into a wide variety of species. As another example, a manoyl oxide biosynthesis gene cluster can be combined such that each manoyl oxide pathway coding sequence is operably linked to a separate regulatory region, to form a manoyl oxide pathway module. Such a module can be used in those species for which monocistronic expression is necessary or desirable. In addition to genes useful for manoyl oxide production, a recombinant construct typically also contains an origin of replication, and one or more selectable markers for maintenance of the construct in appropriate species.

It will be appreciated that because of the degeneracy of the genetic code, a number of nucleic acids can encode a particular polypeptide; i.e., for many amino acids, there is more than one nucleotide triplet that serves as the codon for the amino acid. Thus, codons in the coding sequence for a given polypeptide can be modified such that optimal expression in a particular host is obtained, using appropriate codon bias tables for that host (e.g., microorganism). As isolated nucleic acids, these modified sequences can exist as purified molecules and can be incorporated into a vector or a virus for use in constructing modules for recombinant nucleic acid constructs.

Host Microorganisms

Recombinant hosts can be used to express polypeptides for the producing manoyl oxide, including mammalian, insect, plant, and algal cells. A number of prokaryotes and eukaryotes are also suitable for use in constructing the recombinant microorganisms described herein, e.g., gram-negative bacteria, yeast, and fungi. A species and strain selected for use as a manoyl oxide production strain is first analyzed to determine which production genes are endogenous to the strain and which genes are not present. Genes for which an endogenous counterpart is not present in the strain are advantageously assembled in one or more recombinant constructs, which are then transformed into the strain in order to supply the missing function(s).

Typically, the recombinant microorganism is grown in a fermenter at a defined temperature(s) for a desired period of time. The constructed and genetically engineered microorganisms provided by the invention can be cultivated using conventional fermentation processes, including, inter alia, chemostat, batch, fed-batch cultivations, semi-continuous fermentations such as draw and fill, continuous perfusion fermentation, and continuous perfusion cell culture. Depending on the particular microorganism used in the method, other recombinant genes such as isopentenyl biosynthesis genes and terpene synthase and cyclase genes may also be present and expressed. Levels of substrates and intermediates, e.g., isopentenyl diphosphate, dimethylallyl diphosphate, GGPP, ent-kaurene and ent-kaurenoic acid, can be determined by extracting samples from culture media for analysis according to published methods.

Carbon sources of use in the instant method include any molecule that can be metabolized by the recombinant host cell to facilitate growth and/or production of the manoyl oxide. Examples of suitable carbon sources include, but are not limited to, sucrose (e.g., as found in molasses), fructose, xylose, ethanol, glycerol, glucose, cellulose, starch, cellobiose or other glucose-comprising polymer. In embodiments employing yeast as a host, for example, carbons sources such as sucrose, fructose, xylose, ethanol, glycerol, and glucose are suitable. The carbon source can be provided to the host organism throughout the cultivation period or alternatively, the organism can be grown for a period of time in the presence of another energy source, e.g., protein, and then provided with a source of carbon only during the fed-batch phase.

After the recombinant microorganism has been grown in culture for the desired period of time, manoyl oxide can then be recovered from the culture using various techniques known in the art. In some embodiments, a permeabilizing agent can be added to aid the feedstock entering into the host and product getting out. For example, a crude lysate of the cultured microorganism can be centrifuged to obtain a supernatant. The resulting supernatant can then be applied to a chromatography column, e.g., a C-18 column, and washed with water to remove hydrophilic compounds, followed by elution of the compound(s) of interest with a solvent such as methanol. The compound(s) can then be further purified by preparative HPLC. See also, WO 2009/140394.

It will be appreciated that the various genes and modules discussed herein can be present in two or more recombinant hosts rather than a single host. When a plurality of recombinant hosts is used, they can be grown in a mixed culture to accumulate manoyl oxide.

Alternatively, the two or more hosts each can be grown in a separate culture medium and the product of the first culture medium, e.g., copal-8-ol diphosphate, can be introduced into second culture medium to be converted into manoyl oxide. In another example, the product of the first culture medium, e.g., manoyl oxide, can be introduced into second culture medium to be converted into a subsequent intermediate, or into an end product such as, for example, forskolin or ambrox. The product produced by the second, or final host is then recovered. It will also be appreciated that in some embodiments, a recombinant host is grown using nutrient sources other than a culture medium and utilizing a system other than a fermenter.

Exemplary prokaryotic and eukaryotic species are described in more detail below. However, it will be appreciated that other species can be suitable. For example, suitable species can be in a genus such as *Agaricus, Aspergillus, Bacillus, Candida, Corynebacterium, Eremothecium, Escherichia, Fusarium/Gibberella, Kluyveromyces, Laetiporus, Lentinus, Phaffia, Phanerochaete, Pichia, Physcomitrella, Rhodoturula, Saccharomyces, Schizosaccharomyces, Sphaceloma, Xanthophyllomyces* or *Yarrowia*. Exemplary species from such genera include *Lentinus tigrinus, Laetiporus sulphureus, Phanerochaete chrysosporium, Pichia pastoris, Cyberlindnera jadinii, Physcomitrella patens, Rhodoturula glutinis, Rhodoturula mucilaginosa, Phaffia rhodozyma, Xanthophyllomyces dendrorhous, Fusarium fujikuroi/Gibberella fujikuroi, Candida utilis, Candida glabrata, Candida albicans,* and *Yarrowia lipolytica*.

In some embodiments, a microorganism can be a prokaryote such as *Escherichia* bacteria cells, for example, *Escherichia coli* cells; *Lactobacillus* bacteria cells; *Lactococcus* bacteria cells; *Cornebacterium* bacteria cells; *Acetobacter* bacteria cells; *Acinetobacter* bacteria cells; or *Pseudomonas* bacterial cells.

In some embodiments, a microorganism can be an Ascomycete such as *Gibberella fujikuroi, Kluyveromyces lactis, Schizosaccharomyces pombe, Aspergillus niger, Yarrowia lipolytica, Ashbya gossypii,* or *S. cerevisiae*.

In some embodiments, a microorganism can be an algal cell such as *Blakeslea trispora, Dunaliella salina, Haematococcus pluvialis, Chlorella* sp., *Undaria pinnatifida, Sargassum, Laminaria japonica, Scenedesmus almeriensis* species.

In some embodiments, a microorganism can be a cyanobacterial cell such as *Blakeslea trispora, Dunaliella salina, Haematococcus pluvialis, Chlorella* sp., *Undaria pinnatifida, Sargassum, Laminaria japonica, Scenedesmus almeriensis*.

*Saccharomyces* spp.

*Saccharomyces* is a widely used chassis organism in synthetic biology, and can be used as the recombinant microorganism platform. For example, there are libraries of mutants, plasmids, detailed computer models of metabolism and other information available for *S. cerevisiae*, allowing for rational design of various modules to enhance product yield. Methods are known for making recombinant *S. cerevisiae* microorganisms. As shown in Example 1, manoyl oxide can be produced in *S. cerevisiae* strains.

*Aspergillus* spp.

*Aspergillus* species such as *A. oryzae, A. niger* and *A. sojae* are widely used microorganisms in food production and can also be used as the recombinant microorganism platform. Nucleotide sequences are available for genomes of *A. nidulans, A. fumigatus, A. oryzae, A. clavatus, A. flavus, A. niger,* and *A. terreus*, allowing rational design and modification of endogenous pathways to enhance flux and increase product yield. Metabolic models have been developed for *Aspergillus*, as well as transcriptomic studies and proteomics studies. *A. niger* is cultured for the industrial production of a number of food ingredients such as citric acid and gluconic acid, and thus species such as *A. niger* are generally suitable for producing manoyl oxide.

*E. coli*

*E. coli*, another widely used platform organism in synthetic biology, can also be used as the recombinant microorganism platform. Similar to *Saccharomyces*, there are libraries of mutants, plasmids, detailed computer models of metabolism and other information available for *E. coli*, allowing for rational design of various modules to enhance product yield. Methods similar to those described above for *Saccharomyces* can be used to make recombinant *E. coli* microorganisms.

*Agaricus, Gibberella,* and *Phanerochaete* spp.

*Agaricus, Gibberella,* and *Phanerochaete* spp. can be useful because they are known to produce large amounts of isoprenoids in culture. Thus, the terpene precursors for producing large amounts of manoyl oxide are already produced by endogenous genes. Thus, modules comprising recombinant genes for manoyl oxide biosynthesis polypeptides can be introduced into species from such genera without the necessity of introducing mevalonate or MEP pathway genes.

*Arxula adeninivorans (Blastobotrys adeninivorans)*

*Arxula adeninivorans* is dimorphic yeast (it grows as budding yeast like the baker's yeast up to a temperature of 42° C., above this threshold it grows in a filamentous form) with unusual biochemical characteristics. It can grow on a wide range of substrates and can assimilate nitrate. It has successfully been applied to the generation of strains that can produce natural plastics or the development of a biosensor for estrogens in environmental samples.

*Yarrowia lipolytica*

*Yarrowia lipolytica* is dimorphic yeast (see *Arxula adeninivorans*) and belongs to the family Hemiascomycetes. The entire genome of *Yarrowia lipolytica* is known. *Yarrowia* species is aerobic and considered to be non-pathogenic. *Yarrowia* is efficient in using hydrophobic substrates (e.g. alkanes, fatty acids, oils) and can grow on sugars. It has a high potential for industrial applications and is an oleaginous microorgamism. *Yarrowia lipolyptica* can accumulate lipid content to approximately 40% of its dry cell weight and is a model organism for lipid accumulation and remobilization. See e.g., Nicaud, 2012, *Yeast* 29(10):409-18; Beopoulos et al., 2009, *Biochimie* 91(6):692-6; Bankar et al., 2009, *Appl Microbiol Biotechnol.* 84(5):847-65.

*Rhodotorula* sp.

*Rhodotorula* is unicellular, pigmented yeast. The oleaginous red yeast, *Rhodotorula glutinis*, has been shown to produce lipids and carotenoids from crude glycerol (Saenge et al., 2011, *Process Biochemistry* 46(1):210-8). *Rhodotorula toruloides* strains have been shown to be an efficient fed-batch fermentation system for improved biomass and lipid productivity (Li et al., 2007, *Enzyme and Microbial Technology* 41:312-7).

*Rhodosporidium toruloides*

*Rhodosporidium toruloides* is oleaginous yeast and useful for engineering lipid-production pathways (See e.g. Zhu et al., 2013, *Nature Commun.* 3:1112; Ageitos et al., 2011, *Applied Microbiology and Biotechnology* 90(4):1219-27).

*Candida boidinii*

*Candida boidinii* is methylotrophic yeast (it can grow on methanol). Like other methylotrophic species such as *Hansenula polymorpha* and *Pichia pastoris*, it provides an excellent platform for producing heterologous proteins. Yields in a multigram range of a secreted foreign protein have been reported. A computational method, IPRO, recently predicted mutations that experimentally switched the cofactor specificity of *Candida boidinii* xylose reductase from NADPH to NADH. See, e.g., Mattanovich et al., 2012, *Methods Mol Biol.* 824:329-58; Khoury et al., 2009, *Protein Sci.* 18(10):2125-38.

*Hansenula polymorpha* (*Pichia angusta*)

*Hansenula polymorpha* is methylotrophic yeast (see *Candida boidinii*). It can furthermore grow on a wide range of other substrates; it is thermo-tolerant and can assimilate nitrate (see also *Kluyveromyces lactis*). It has been applied to producing hepatitis B vaccines, insulin and interferon alpha-2a for the treatment of hepatitis C, furthermore to a range of technical enzymes. See, e.g., Xu et al., 2014, *Virol Sin.* 29(6):403-9.

*Kluyveromyces lactis*

*Kluyveromyces lactis* is yeast regularly applied to the production of kefir. It can grow on several sugars, most importantly on lactose which is present in milk and whey. It has successfully been applied among others for producing chymosin (an enzyme that is usually present in the stomach of calves) for producing cheese. Production takes place in fermenters on a 40,000 L scale. See, e.g., van Ooyen et al., 2006, *FEMS Yeast Res.* 6(3):381-92.

*Pichia pastoris*

*Pichia pastoris* is methylotrophic yeast (see *Candida boidinii* and *Hansenula polymorpha*). It provides an efficient platform for producing foreign proteins. Platform elements are available as a kit and it is worldwide used in academia for producing proteins. Strains have been engineered that can produce complex human N-glycan (yeast glycans are similar but not identical to those found in humans). See, e.g., Piirainen et al., 2014, *N Biotechnol.* 31(6):532-7.

*Physcomitrella* spp.

*Physcomitrella* mosses, when grown in suspension culture, have characteristics similar to yeast or other fungal cultures. This genera can be used for producing plant secondary metabolites, which can be difficult to produce in other types of cells.

Table 1 indicates the identities of the sequences utilized herein.

TABLE 1

Sequences used herein.

| SEQ ID NO | Sequence Description |
|---|---|
| SEQ ID NO: 1 | Codon-optiminzed nucleotide sequence encoding *Synechococcus* sp. GGPPS7 |
| SEQ ID NO: 2 | Amino acid sequence of *Synechococcus* sp. GGPPS7 |
| SEQ ID NO: 3 | Codon-optiminzed nucleotide sequence encoding *Aspergillus nidulans* GGPPS10 |
| SEQ ID NO: 4 | Amino acid sequence of *Aspergillus nidulans* GGPPS10 |
| SEQ ID NO: 5 | Wildtype nucleotide sequence encoding *Coleus forskohlii* TPS2 (CfTPS2) |
| SEQ ID NO: 6 | Amino acid sequence of CfTPS2 |
| SEQ ID NO: 7 | Codon-optimized nucleotide sequence encoding CfTPS2 |
| SEQ ID NO: 8 | Wildtype nucleotide sequence encoding *Coleus forskohlii* TPS3 (CfTPS3) |
| SEQ ID NO: 9 | Amino acid sequence of CfTPS3 |
| SEQ ID NO: 10 | Codon-optimized nucleotide sequence encoding CfTPS3 |
| SEQ ID NO: 11 | Amino acid sequence of *Coleus forskohlii* TPS4 (CfTPS4) |
| SEQ ID NO: 12 | Wildtype nucleotide sequence encoding CfTPS4 |

The invention will be further described in the following examples, which do not limit the scope of the invention described in the claims.

EXAMPLES

The Examples that follow are illustrative of specific embodiments of the invention, and various uses thereof. They are set forth for explanatory purposes only and are not to be taken as limiting the invention.

Example 1: Production of Manoyl Oxide in *S. cerevisiae*

TPS2 (SEQ ID NO:6), TPS3 (SEQ ID NO:9), *Synechococcus* sp. GGPPS7 (SEQ ID NO:2), and *A. nidulans* GGPPS10 (SEQ ID NO:4) were codon-optimized for expression in *S. cerevisiae*. The strains produced are shown in Table 2.

TABLE 2

Genes in Manoyl Oxide Producing Strains.

| Strain | GGPPS | TPS2 | TPS3 |
|---|---|---|---|
| 1 | GGPPS7 (SEQ ID NO: 1, SEQ ID NO:2) | codon-optimized CfTPS2 (SEQ ID NO: 6, SEQ ID NO: 7) wildtype CfTPS2 (SEQ ID NO: 5, SEQ ID NO: 6) | codon-optimized CfTPS3 (SEQ ID NO: 9, SEQ ID NO: 10) wildtype CfTPS3 (SEQ ID NO: 8, SEQ ID NO: 9) |

TABLE 2-continued

Genes in Manoyl Oxide Producing Strains.

| Strain | GGPPS | TPS2 | TPS3 |
|---|---|---|---|
| 2 | GGPPS7 (SEQ ID NO: 1, SEQ ID NO: 2) | codon-optimized CfTPS2 (SEQ ID NO: 6, SEQ ID NO: 7) | codon-optimized CfTPS3 (SEQ ID NO: 9, SEQ ID NO: 10) |
| 3 | GGPPS10 (SEQ ID NO: 3, SEQ ID NO: 4) | codon-optimized CfTPS2 (SEQ ID NO: 6, SEQ ID NO: 7) wildtype CfTPS2 (SEQ ID NO: 5, SEQ ID NO: 6) | codon-optimized CfTPS3 (SEQ ID NO: 9, SEQ ID NO: 10) wildtype CfTPS3 (SEQ ID NO: 8, SEQ ID NO: 9) |
| 4 | GGPPS10 (SEQ ID NO: 3, SEQ ID NO: 4) | codon-optimized CfTPS2 (SEQ ID NO: 6, SEQ ID NO: 7) | codon-optimized CfTPS3 (SEQ ID NO: 9, SEQ ID NO: 10) |
| 5 | GGPPS7 (SEQ ID NO: 1, SEQ ID NO: 2) | codon-optimized CfTPS2 (SEQ ID NO: 6, SEQ ID NO: 7) wildtype CfTPS2 (SEQ ID NO: 5, SEQ ID NO: 6) | codon-optimized CfTPS3 (SEQ ID NO:9, SEQ ID NO: 10) wildtype CfTPS3 (SEQ ID NO: 8, SEQ ID NO: 9) |
| 6 | GGPPS7 (SEQ ID NO: 1, SEQ ID NO: 2) | codon-optimized CfTPS2 (SEQ ID NO: 6, SEQ ID NO: 7) wildtype CfTPS2 (SEQ ID NO: 5, SEQ ID NO: 6) | codon-optimized CfTPS3 (SEQ ID NO: 9, SEQ ID NO: 10) |
| 7 | GGPPS10 (SEQ ID NO: 3, SEQ ID NO: 4) | codon-optimized CfTPS2 (SEQ ID NO: 6, SEQ ID NO: 7) wildtype CfTPS2 (SEQ ID NO: 5, SEQ ID NO: 6) | codon-optimized CfTPS3 (SEQ ID NO: 9, SEQ ID NO: 10) wildtype CfTPS3 (SEQ ID NO: 8, SEQ ID NO: 9) |
| 8 | GGPPS10 (SEQ ID NO: 3, SEQ ID NO: 4) | codon-optimized CfTPS2 (SEQ ID NO: 6, SEQ ID NO: 7) | codon-optimized CfTPS3 (SEQ ID NO: 9, SEQ ID NO: 10) |
| 9 | GGPPS7 (SEQ ID NO: 1, SEQ ID NO: 2) | codon-optimized CfTPS2 (SEQ ID NO: 6, SEQ ID NO: 7) wildtype CfTPS2 (SEQ ID NO: 5, SEQ ID NO: 6) | codon-optimized CfTPS3 (SEQ ID NO: 9, SEQ ID NO: 10) wildtype CfTPS3 (SEQ ID NO: 8, SEQ ID NO: 9) |
| 10 | GGPPS7 (SEQ ID NO: 1, SEQ ID NO: 2) | codon-optimized CfTPS2 (SEQ ID NO: 6, SEQ ID NO: 7) | codon-optimized CfTPS3 (SEQ ID NO: 9, SEQ ID NO: 10) |
| 11 | GGPPS10 (SEQ ID NO: 3, SEQ ID NO: 4) | codon-optimized CfTPS2 (SEQ ID NO: 6, SEQ ID NO: 7) wildtype CfTPS2 (SEQ ID NO: 5, SEQ ID NO: 6) | codon-optimized CfTPS3 (SEQ ID NO: 9, SEQ ID NO: 10) wildtype CfTPS3 (SEQ ID NO: 8, SEQ ID NO: 9) |
| 12 | GGPPS10 (SEQ ID NO: 3, SEQ ID NO: 4) | codon-optimized CfTPS2 (SEQ ID NO: 6, SEQ ID NO: 7) | codon-optimized CfTPS3 (SEQ ID NO: 9, SEQ ID NO: 10) |

A single colony of each strain was inoculated into 500 µL SC-Ura in a 2.2 mL well of a 96 deep well plate. Colonies were grown overnight at 30° C., 400 RPM shaking. 50 µL of each culture were then used to inoculate 500 µL DELFT media, and the cultures were grown for an additional 72 h at 30° C., 400 RPM shaking.

Metabolites were extracted from the culture broth by adding 500 µL 96% ethanol and incubating at 78° C. for 10 min before transferring the samples to fresh tubes and centrifuging at 15,000 g for min. 500 µL of the supernatant was then transferred to a GC vial and was two-phase extracted with 500 mL hexane. Following extraction, each solvent was transferred into new 1.5-mL glass vials and stored at −20° C. For GC-MS analysis, 1 µL of each hexane extract was injected into a Shimadzu GC-MS-QP2010 Ultra. Separation was carried out using an Agilent HP-5MS column (20 m×0.180 mm i.d., 0.18 µm film thickness) with purge flow of 4 mL/min for 1 min, using $H_2$ as carrier gas. The GC temperature program was as follows: 60° C. for 1 min, ramp at 30° C./min to 180° C., ramp at 10° C./min to 250° C., ramp at 30° C./min to 320° C., and hold for 3 min. Injection temperature was set at 250° C. in splitless mode. Column flow and pressure were set to 5 mL/min and 66.7 kPa, respectively, yielding a linear velocity of 66.5 cm/s. The ion source and MS transfer line were set to 300° C. and 280° C., respectively. MS was set in scan mode from m/z 50 to m/z 350 with a scan width of 0.5 s; solvent cut-off was 4 min.

A representative GC-MS trace of 13R-manoyl oxide produced in an *S. cerevisiae* strain comprising GGPPS7

Figure 3:
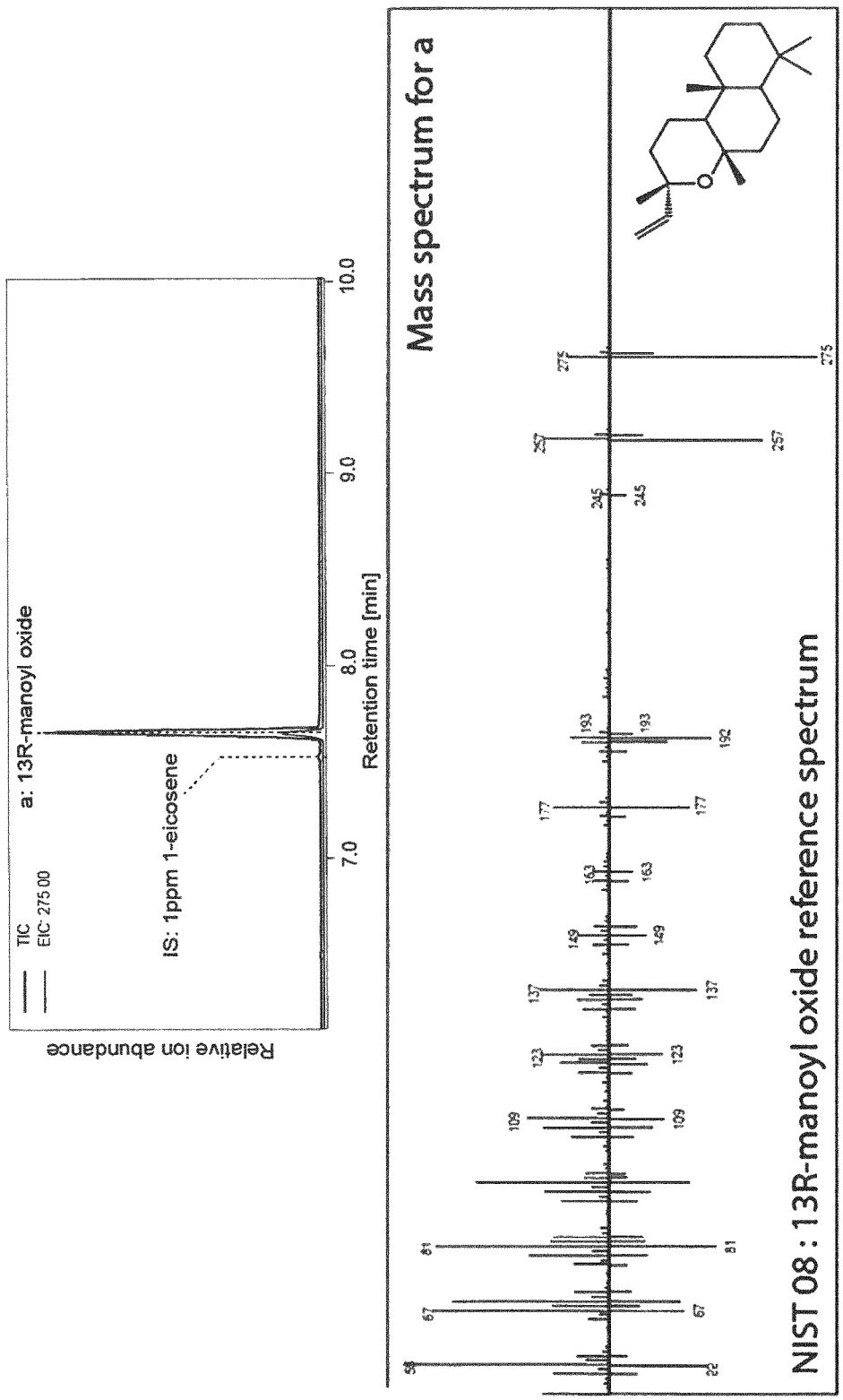
FIG. 3 shows a Gas Chromatography Mass Spectrometry (GC-MS) trace and Mass Spectrometry (MS) spectrum of 13R-manoyl oxide from an *S. cerevisiae* strain comprising GGPPS7 (SEQ ID NO:1, SEQ ID NO:2), codon-optimized CfTPS2 (SEQ ID NO:6, SEQ ID NO:7), and codon-optimized CfTPS3 (SEQ ID NO:9, SEQ ID NO:10).
Figure 4:
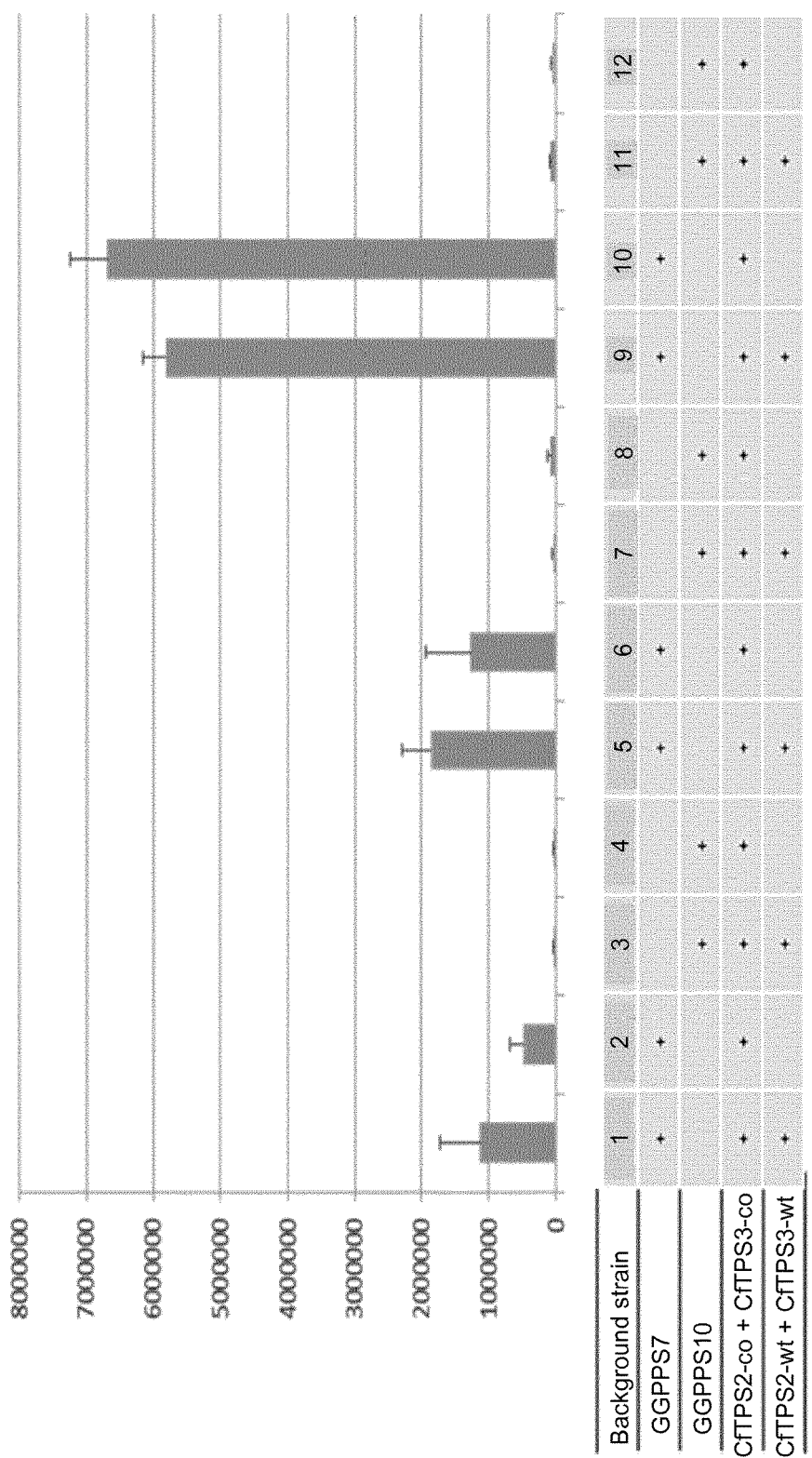
FIG. 4 shows manoyl oxide extractions from *S. cerevisiae* strains expressing i) GGPPS7 (SEQ ID NO:1, SEQ ID NO:2) or GGPPS10 (SEQ ID NO:3, SEQ ID NO:4), i) codon-optimized *C. forskohlii* TPS2 (CfTPS2) (SEQ ID NO:6, SEQ ID NO:7) and/or wildtype CfTPS2 (SEQ ID NO:5, SEQ ID NO:6), and iii) codon-optimized *C. forskohlii* TPS3 (CfTPS3) (SEQ ID NO:9, SEQ ID NO:10) and/or wildtype CfTPS3 (SEQ ID NO:8, SEQ ID NO:9).

(SEQ ID NO:1, SEQ ID NO:2), codon-optimized CfTPS2 (SEQ ID NO:6, SEQ ID NO:7), and codon-optimized CfTPS3 (SEQ ID NO:9, SEQ ID NO:10) is shown in FIG. 3. Manoyl oxide was produced in each of the strains tested. It was also shown that manoyl oxide was produced in all the different background yeast strains 1-12, with highest levels found in background strains 9-12 (FIG. 4). The manoyl oxide levels in strains 9-12 were found to be up to 6- and 3.5-fold higher than in strains 1-4 and strains 5-8, respectively (FIG. 4). Strains comprising GGPPS7 (SEQ ID NO:1, SEQ ID NO:2) produced up to 150-fold more manoyl oxide, compared to strains comprising GGPPS10 (SEQ ID NO:3, SEQ ID NO:4). See strains 10 and 12 in FIG. 4.

Having described the invention in detail and by reference to specific embodiments thereof, it will be apparent that modifications and variations are possible without departing from the scope of the invention defined in the appended claims. More specifically, although some aspects of the present invention are identified herein as particularly advantageous, it is contemplated that the present invention is not necessarily limited to these particular aspects of the invention.

TABLE 3

Sequences disclosed herein.

```
SEQ ID NO: 1
atggtcgcac aaactttcaa cctggatacc tacttatccc aaagacaaca acaagttgaa    60
gaggccctaa gtgctgctct tgtgccagct tatcctgaga gaatatacga agctatgaga   120
tactccctcc tggcaggtgg caaaagatta agacctatct tatgtttagc tgcttgcgaa   180
ttggcaggtg gttctgttga acaagccatg ccaactgcgt gtgcacttga aatgatccat   240
acaatgtcac taattcatga tgacctgcca gccatggata acgatgattt cagaagagga   300
aagccaacta atcacaaggt gttcggggaa gatatagcca tcttagcggg tgatgcgctt   360
ttagcttacg cttttgaaca tattgcttct caaacaagag gagtaccacc tcaattggtg   420
ctacaagtta ttgctagaat cggacacgcc gttgctgcaa caggcctcgt tggaggccaa   480
gtcgtagacc ttgaatctga aggtaaagct atttccttag aaacattgga gtatattcac   540
tcacataaga ctggagcctt gctggaagca tcagttgtct caggcggtat tctcgcaggg   600
gcagatgaag agcttttggc cagattgtct cattacgcta gagatatagg cttggctttt   660
caaatcgtcg atgatatcct ggatgttact gctacatctg aacagttggg gaaaaccgct   720
ggtaaagacc aggcagccgc aaaggcaact tatccaagtc tattgggttt agaagcctct   780
agacagaaag cggaagagtt gattcaatct gctaaggaag ccttaagacc ttacggttca   840
caagcagagc cactcctagc gctggcagac ttcatcacac gtcgtcagca ttaa          894

SEQ ID NO: 2
MVAQTFNLDT YLSQRQQQVE EALSAALVPA YPERIYEAMR YSLLAGGKRL RPILCLAACE    60
LAGGSVEQAM PTACALEMIH TMSLIHDDLP AMDNDDFRRG KPTNHKVFGE DIAILAGDAL   120
LAYAFEHIAS QTRGVPPQLV LQVIARIGHA VAATGLVGGQ VVDLESEGKA ISLETLEYIH   180
SHKTGALLEA SVVSGGILAG ADEELLARLS HYARDIGLAF QIVDDILDVT ATSEQLGKTA   240
GKDQAAAKAT YPSLLGLEAS RQKAEELIQS AKEALRPYGS QAEPLLALAD FITRRQH     297

SEQ ID NO: 3
atgacgtccg attcgcactt tcaccctccg cacgcaatac cacccaggat tagctccaac    60
cgaatgtcag gtgcatctac tcgagacaag gcagcactaa tgggaaactt cgagaaggac   120
tggctgtcaa aaggtgacaa gcttcagaca aacaccgatt tgtctaaaag acacacgcga   180
aatcagtcaa gtctcgacgg gacaaaatac aaagatggga atggtcccca agagaatgag   240
gaggtgatca tgggtccgta cgactacatg ctgcaacacc cggggaagga cctgcgacgg   300
cagatgatca acgcttttaa cgtatggttg aaggtgccat ctgagagcct ggccatcatc   360
accaaagtag tggctatgct ccataccgct tcattattga tcgacgacgt cgaagacaac   420
tctcttctcc ggcgaggaat tccggtcgca catagcatct atggcaccgc gcagacgatc   480
aattcggcaa actacgttta cttcctcgcc ctccaggagg tgcaaaaact gaagagtccg   540
gcagctatcg acatatacgt ccaggagctg ctgaatttac acagagggca aggcatggat   600
```

TABLE 3-continued

Sequences disclosed herein.

```
ctgttctggc gagacacgct cacttgtcca agcgaagatg aatacttgga gatggtgggc    660
aacaagactg gaggtttgtt ccggctagct gtgaaattga tgcaagctga aagcagcact    720
ggaaaggact gtgtggccct tgtgaatgtt ttgggactgg tctttcagat atgcgacgac    780
tatctcaatt tatccgacac gacgtatacc cagaacaaag gctctgtga agacctcaca     840
gagggcaaat tttcattccc cattatccac agcattcgat cgaacccggg gaaccatcag    900
ctcatcaata tcctccggca gagaacaaag gatgaagaag tcaaacgcta cgcgctccag    960
tatatgaaaa gcacgggcag tttcaagcat acgcaggatg ttgttcggca gctacgtgcc   1020
agagctctgc agctcattga agagattgag aacagcgaaa atggcgagca accggaggaa   1080
cacaatgacg gtacgatggt ccgggcaatc ctcgataaaa tcacagaatc caccttggct   1140
gatacgaata cgactacgag agatatcaac ggcaactgtg cgacccgtta a            1191
```

SEQ ID NO: 4
```
MTSDSHFHPP HAIPPRISSN RMSGASTRDK AALMGNFEKD WLSKGDKLQT NTDLSKRHTR     60
NQSSLDGTKY KDGKWSQENE EVIMGPYDYM LQHPGKDLRR QMINAFNVWL KVPSESLAII   120
TKVVAMLHTA SLLIDDVEDN SLLRRGIPVA HSIYGTAQTI NSANYVYFLA LQEVQKLKSP   180
AAIDIYVQEL LNLHRGQGMD LFWRDTLTCP SEDEYLEMVG NKTGGLFRLA VKLMQAESST   240
GKDCVALVNV LGLVFQICDD YLNLSDTTYT QNKGLCEDLT EGKFSFPIIH SIRSNPGNHQ   300
LINILRQRTK DEEVKRYALQ YMESTGSFKH TQDVVRQLRA RALQLIEEIE NSENGEQPEE   360
HNDGTMVRAI LDKITESTLA DTNTTTRDIN GNCATR                             396
```

SEQ ID NO: 5
```
atgagtcgag ttgcaagtct ggatgcgttg aatggaattc aaaaagtcgg cccagccacc     60
attgggactc ctgaagagga aaataaaaag attgaggatt ccattgagta cgtgaaggag   120
ttgttgaaga caatgggcga cgggcgaatc agcgtttccc cgtacgacac agcaatagtt   180
gccctgatta aggacttgga aggaggtgat ggaccagagt ttccatcttg tctagagtgg   240
attgcacaga tcaactggc tgatggttct tggggggatc acttcttctg tatttatgat   300
cgggttgtta atacagcagc ttgtgtggtc gccttaaagt cgtggaacgt tcacgcagac   360
aagattgaga aaggagcagt gtacctgaag gagaatgtgc ataaacttaa agatgggaag   420
attgagcaca tgcccgcagg gtttgaattt gtggttcctg ccactcttga aagagccaaa   480
gccttgggga tcaaaggtct tccctatgat gatcctttca tcagggaaat ttatagtgca   540
aaacaaacaa gattgaccaa gataccaaag ggcatgatct acgaatctcc aacttcttta   600
ttatatagtt tagacggtct ggaaggcttg gagtgggaca agatactgaa actgcagtcg   660
gccgatggct cattcatcac ctctgtgtcg tctactgcct tcgtattcat gcacaccaac   720
gaccttaaat gccacgcctt catcaaaaat gccctcacca attgcaacgg gggagtaccc   780
cacacgtatc cagtggatat cttcgcacga ctttgggcag tggaccgact gcaacgcctc   840
ggaatatctc gattctttga gcctgagatc aaatatttaa tggatcacat caataacgtg   900
tgagggagaga agggagtttt cagttcaagg cattcacaat ttgcggatat tgacgacaca   960
tccatgggca tcaggcttct gaaaatgcac ggatacaatg tcaacccaaa tgcacttgaa  1020
catttcaaac agaagatgg gaagtttaca tgctatgctg atcaacatat cgagtctcca  1080
tcccccatgt acaatctcta cagggctgct cagcttcgtt ttccaggaga gaaaattctt  1140
caacaagccc ttcaatttgc ctataatttt tacatgaaaa acctagccag caatcacttt  1200
caagaaaaat gggtcatatc cgaccaccta attgatgagg taaggatcgg gctgaagatg  1260
```

TABLE 3-continued

Sequences disclosed herein.

| | | | | |
|---|---|---|---|---|
| ccatggtacg | ccaccctacc | gcgagtggag | gcttcatact | atcttcaaca ttatggtgga | 1320 |
| tccagcgacg | tatggattgg | caaaacttta | tacagaatgc | cagaaatcag taacgacaca | 1380 |
| tacaaaatac | ttgcacaatt | ggacttcaac | aaatgtcaag | cacaacatca gttggaatgg | 1440 |
| atgtccatga | aagagtggta | tcaaagtaat | aatgttaaag | aatttgggat aagcaagaaa | 1500 |
| gaacttcttc | ttgcttactt | tttggctgct | gcaaccatgt | ttgaacccga acgcacacaa | 1560 |
| gagaggatta | tgtgggcgaa | aactcaagtc | tttctcggag | tgatcacatc atttctcaac | 1620 |
| aaagaaaaca | caatgtcatt | cgacctaaag | attgcacttt | taccccaacc ccaacatcaa | 1680 |
| ataaatggtt | ctgagatgaa | gaatggactt | gctcaaactc | ttcctgcagc cttccgacaa | 1740 |
| ctactcaagg | aattcgacaa | atacacaaga | catcaattga | ggaatacttg aacaaatgg | 1800 |
| ttgatgaaac | tgaagcaagg | agatgacaat | ggcggcgcag | atgcagagct ccttgcaaac | 1860 |
| acattaaaca | tatgtgctgg | acataacgaa | gacatattat | cgcactatga atacaccgct | 1920 |
| ctctcctccc | tcacaaacaa | aatatgtcag | cgtctaagtc | aaattcaaga taaaaagatg | 1980 |
| ctggaaattg | aggaggggag | cataaaagat | aaggagatgg | agctcgaaat acaaacattg | 2040 |
| gtgaagttag | tcctccaaga | aaccagtggg | ggtatcgata | gaaacatcaa gcaaacattt | 2100 |
| ttatcagtat | tcaagacatt | ttactacagg | gcctaccacg | atgctaagac tatcgatgcc | 2160 |
| catatttccc | aagtactatt | tgaaccagtg | gtctga | | 2196 |

SEQ ID NO: 6
| | | | | | |
|---|---|---|---|---|---|
| MSRVASLDAL | NGIQKVGPAT | IGTPEEENKK | IEDSIEYVKE | LLKTMGDGRI | SVSPYDTAIV | 60 |
| ALIKDLEGGD | GPEFPSCLEW | IAQNQLADGS | WGDHFFCIYD | RVVNTAACVV | ALKSWNVHAD | 120 |
| KIEKGAVYLK | ENVHKLKDGK | IEHMPAGFEF | VVPATLERAK | ALGIKGLPYD | DPFIREIYSA | 180 |
| KQTRLTKIPK | GMIYESPTSL | LYSLDGLEGL | EWDKILKLQS | ADGSFITSVS | STAFVFMHTN | 240 |
| DLKCHAFIKN | ALTNCGGVP | HTYPVDIFAR | LWAVDRLQRL | GISRFFEPEI | KYLMDHINNV | 300 |
| WREKGVFSSR | HSQFADIDDT | SMGIRLLKMH | GYNVNPNALE | HFKQKDGKFT | CYADQHIESP | 360 |
| SPMYNLYRAA | QLRFPGEEIL | QQALQFAYNF | LHENLASNHF | QEKWVISDHL | IDEVRIGLKM | 420 |
| PWYATLPRVE | ASYYLQHYGG | SSDVWIGKTL | YRMPEISNDT | YKILAQLDFN | KCQAQHQLEW | 480 |
| MSMKEWYQSN | NVKEFGISKK | ELLLAYFLAA | ATMFEPERTQ | ERIMWAKTQV | VSRMITSFLN | 540 |
| KENTMSFDLK | IALLTQPQHQ | INGSEMKNGL | AQTLPAAFRQ | LLKEFDKYTR | HQLRNTWNKW | 600 |
| LMKLKQGDDN | GGADAELLAN | TLNICAGHNE | DILSHYEYTA | LSSLTNKICQ | RLSQIQDKKM | 660 |
| LEIEEGSIKD | KEMELEIQTL | VKLVLQETSG | GIDRNIKQTF | LSVFKTFYYR | AYHDAKTIDA | 720 |
| HIFQVLFEPV | V | | | | | 731 |

SEQ ID NO: 7
| | | | | |
|---|---|---|---|---|
| atgtccagag | ttgcttcctt | ggatgctttg | aatggtattc | aaaaagttgg tccagctacc | 60 |
| attggtactc | cagaagaaga | aaacaagaag | atcgaagatt | ccatcgaata cgtcaaagaa | 120 |
| ttattgaaaa | ccatgggtga | cggtagaatc | tctgtttctc | catatgatac tgctatcgtc | 180 |
| gccttgatta | aggatttgga | aggtggtgat | ggtccagaat | tccatcttg tttggaatgg | 240 |
| attgcccaaa | atcaattggc | tgatggttct | tggggtgatc | attttttctg tatctacgat | 300 |
| agagttgtta | acaccgctgc | ttgtgttgtt | gctttgaaat | cttggaatgt tcacgccgat | 360 |
| aagattgaaa | aaggtgccgt | tactgaa | gaaaacgtcc | acaaattgaa ggacggtaag | 420 |
| atagaacata | tgccagctgg | ttttgaattc | gttgttccag | caactttgga aagagctaaa | 480 |
| gctttgggta | ttaagggttt | gccatatgat | gatccattca | tcagagaaat ctactccgct | 540 |

TABLE 3-continued

Sequences disclosed herein.

| | |
|---|---|
| aagcaaacta gattgactaa gattccaaag ggtatgatct acgaatctcc aacctctttg | 600 |
| ttgtactctt tggatggttt agaaggtttg gaatgggata agatcttgaa gttgcaatca | 660 |
| gctgacggtt ctttcatcac ttctgttct tctactgcct tcgttttcat gcataccaac | 720 |
| gatttgaagt gccatgcctt tattaagaac gctttgacta actgtaatgg tggtgttcca | 780 |
| catacttacc cagttgatat ttttgctaga ttgtgggccg ttgacagatt gcaaagattg | 840 |
| ggtatttcta gattcttcga accagaaatc aaatacttga tggaccacat caacaacgtt | 900 |
| tggagagaaa agggtgtttt ctcatccaga cattctcaat cgccgatat tgatgatacc | 960 |
| tccatgggta tcagattatt gaagatgcat ggttacaacg ttaacccaaa cgctttggaa | 1020 |
| catttcaagc aaaaggatgg taaattcacc tgttacgccg atcaacatat tgaatctcca | 1080 |
| tctccaatgt ataacttgta cagagctgcc caattgagat ttccaggtga agaaatttta | 1140 |
| caacaagcct tgcaattcgc ctacaacttc ttgcacgaaa atttggcttc taaccacttc | 1200 |
| caagaaaagt gggttatctc cgatcatttg atcgatgaag ttagaatcgg tttgaaaatg | 1260 |
| ccatggtatg ctactttgcc aagagttgaa gcttcttact acttgcaaca ttacggtggt | 1320 |
| tcttccgatg tttggattgg taaaaccttg tatagaatgc cagaaatctc taacgacacc | 1380 |
| tacaagattt tggctcaatt ggatttcaac aagtgccaag ctcaacatca attagaatgg | 1440 |
| atgtctatga aggaatggta tcaatccaac aacgtaaaag aattcggtat ctccaagaaa | 1500 |
| gaattgttgt tggcttactt tttggctgct gctactatgt ttgaacctga agaactcaa | 1560 |
| gaaagaatca tgtgggctaa gacccaagtt gtttctagaa tgattacctc attcttgaac | 1620 |
| aaagaaaaca ctatgtcctt cgacttgaag attgctttgt tgactcaacc acaacaccaa | 1680 |
| atcaatggtt ccgaaatgaa gaatggtttg gcacaaactt taccagctgc cttcagacaa | 1740 |
| ttattgaaag aattcgacaa gtacaccaga caccaattga gaaatacttg gaacaagtgg | 1800 |
| ttgatgaagt tgaagcaagg tgatgataac ggtggtgctg atgctgaatt attggctaac | 1860 |
| actttgaaca tttgcgccgg tcataacgaa gatattttgt cccattacga atacaccgcc | 1920 |
| ttgtcatctt tgaccaacaa gatttgtcaa agattgtccc aaatccaaga taagaagatg | 1980 |
| ttggaaatcg aagaaggttc catcaaggac aaagaaatgg aattggaaat tcaaaccttg | 2040 |
| gtcaagttgg tattgcaaga aacttctggt ggtatcgaca gaaacatcaa gcaaactttc | 2100 |
| ttgtccgttt tcaagacctt ctactacaga gcttaccatg atgctaagac cattgatgcc | 2160 |
| catatcttcc aagttttgtt cgaacctgtt gtttaa | 2196 |
| SEQ ID NO: 8 | |
| atgatcacct ctaaatcatc tgcagctgtt aaatgcagcc tcaccacgcc aacagatttg | 60 |
| atggggaaaa taaagagggt cttcaacagg gaagtcgata cttctccggc agccatgact | 120 |
| actcattcta cagatatacc ctctaatctc tgcataatcg acaccctcca gaggctggga | 180 |
| atcgaccaat acttccaatc cgaaatcgac gctgttctac atgatacata caggttatgg | 240 |
| caactgaaaa agaaagatat attttcggat attactactc atgcaatggc gttcagactt | 300 |
| ttgcgagtca aaggatatga agttgcatca gacgaactgg ctccatacgc tgatcaagag | 360 |
| cgcattaacc tgcaaaccat tgatgtgccg acagttgttg agctatacag agcagcacag | 420 |
| gagagattaa ctgaagaaga tagcactctt gagaaactgt atgtttggac cagcgccttt | 480 |
| ctgaagcagc agttgctcac tgatgccatt cctgacaaga aattgcacaa acaagtggaa | 540 |
| tactacttga agaactacca tggcatatta gatagaatgg gagtgagacg aaacctcgac | 600 |
| ctatatgaca taagccatta taaaagtctc aaagctgctc acaggttcta taatctgagt | 660 |

TABLE 3-continued

Sequences disclosed herein.

```
aatgaagata tcctagcatt tgcgaggcaa gattttaata ttagccaagc ccaacaccag    720
aaagaacttc agcagctgca aaggtggtat gcagattgta ggttggacac gttgaaattt    780
ggaagagatg tagtgcgtat aggaaatttt ctgacttcag caatgattgg tgatcctgaa    840
ttgtctgacc tccgtctagc gtttgccaaa catatagtgc tcgtaacacg tattgatgat    900
tttttcgatc acggtgggcc taagaagaa tcatacgaga tccttgaatt agtaaaagaa     960
tggaaagaga agccagcagg agaatatgtt tctgaagaag ttgaaatcct atttacagca   1020
gtatacaata cagtaaacga gttggcagaa atggctcata tcgaacaagg acgaagcgtt   1080 aaagacctc agttaaactg gtgggttgaa atactatcag ttttcagaat agaattggat    1140
acatggacca acgacacagc acttacctta gaagagtact tgtcacaatc ctgggtgtcc   1200
attggctgca gaatctgcat tctcatatca atgcaattcc aaggtgtaaa attatctgat   1260
gaaatgcttc agagtgaaga atgcactgat ttgtgtcggt atgtttcaat ggttgaccgg   1320
ctgctcaacg atgtgcaaac ttttgagaag gaacgcaagg aaaatacagg aaatagtgtg   1380
agccttctgc aagcagctca caaagatgaa agagtcatta tgaagagga agcttgtata    1440 aaggtaaaag aattggctga atataacagg agaaaactga tgcagattgt ctacaaaaca   1500
ggaaccattt tcccaagaaa atgcaaagat ctgtttttga aggcatgcag aattggttgt   1560
tatttgtact caagtggcga cgaatttact tcgcctcaac aaatgatgga agatatgaag   1620
tcactggttt atgaaccct accaatttct cctcctgaag ctaataatgc aagtggagaa   1680 aaaa gag gtgtcagcaa ctag                                           1704
```

SEQ ID NO: 9
```
MITSKSSAAV KCSLTTPTDL MGKIKEVFNR EVDTSPAAMT THSTDIPSNL CIIDTLQRLG     60

IDQYFQSEID AVLHDTYRLW QLKKKDIFSD ITTHAMAFRL LRVKGYEVAS DELAPYADQE   120

RINLQTIDVP TVVELYRAAQ ERLTEEDSTL EKLYVWTSAF LKQQLLTDAI PDKKLHKQVE   180

YYLKNYHGIL DRMGVRRNLD LYDISHYKSL KAAHRFYNLS NEDILAFARQ DFNISQAQHQ   240

KELQQLQRWY ADCRLDTLKF GRDVVRIGNF LTSAMIGDPE LSDLRLAFAK HIVLVTRIDD   300

FFDHGGPKEE SYEILELVKE WKEKPAGEYV SEEVEILFTA VYNTVNELAE MAHIEQGRSV   360

KDLLVKLWVE ILSVFRIELD TWTNDTALTL EEYLSQSWVS IGCRICILIS MQFQGVKLSD   420

EMLQSEECTD LCRYVSMVDR LLNDVQTFEK ERKENTGNSV SLLQAAHKDE RVINEEEACI   480

KVKELAEYNR RKLMQIVYKT GTIFPRKCKD LFLKACRIGC YLYSSGDEFT SPQQMMEDMK   540

SLVYEPLPIS PPEANNASGE KMSCVSN                                       567
```

SEQ ID NO: 10
```
atgatcacct ccaaatcttc cgctgctgtt aagtgttctt tgactactcc aactgatttg     60
atgggtaaga tcaaagaagt tttcaacaga gaagttgata cctctccagc tgctatgact   120
actcattcta ctgatattcc atccaacttg tgcatcatcg ataccttgca agattgggt    180 atcgaccaat acttccaatc cgaaattgat gctgtcttgc atgatactta cagattgtgg   240
caattgaaga gaaaggacat cttctctgat attaccactc atgctatggc cttcagatta   300
ttgagagtta agggttacga agttgcctct gatgaattgg ctccatatgc tgatcaagaa   360
agaatcaact gcaaaccat tgatgttcca accgtcgtcg aattatacag agctgcacaa   420
gaaagattga ccgaagaaga ttctaccttg gaaagttgt acgtttggac ttctgctttc    480
ttgaagcaac aattattgac cgatgccatc ccagataaga gttgcataa gcaagtcgaa    540 tattacttga gaaactacca cggtatcttg gatagaatgg gtgttagaag aaacttggac   600
```

TABLE 3-continued

Sequences disclosed herein.

```
ttgtacgata tctcccacta caaatctttg aaggctgctc atagattcta caacttgtct      660
aacgaagata ttttggcctt cgccagacaa gatttcaaca tttctcaagc ccaacaccaa      720
aaagaattgc aacaattgca aagatggtac gccgattgca gattggatac tttgaaattc      780
ggtagagatg tcgtcagaat cggtaacttt ttaacctctg ctatgatcgg tgatccagaa      840
ttgtctgatt tgagattggc ttttgctaag cacatcgttt tggttaccag aatcgatgat      900
ttcttcgatc atggtggtcc aaaagaagaa tcctacgaaa ttttggaatt ggtcaaagaa      960
tggaaagaaa agccagctgg tgaatacgtt tctgaagaag tcgaaatctt attcaccgct     1020
gtttacaaca ccgttaacga attggctgaa atggcccata ttgaacaagg tagatctgtt     1080
aaggatttgt tggttaagtt gtgggtcgaa atattgtccg ttttcagaat cgaattggat     1140
acctggacta cgatactgc tttgactttg aagaatact tgtcccaatc ctgggtttct       1200
attggttgca gaatctgcat tttgatctcc atgcaattcc aaggtgttaa gttgagtgac     1260
gaaatgttgc aaagtgaaga atgtaccgat tgtgcagat acgtttccat ggtcgataga     1320
ttattgaacg atgtccaaac cttcgaaaaa gaaagaaaag aaaacaccgg taactccgtt     1380
tctttgttgc aagctgctca caaagacgaa agagttatca cgaagaaga agcctgcatc     1440 aaggtaaaag aattagccga atacaataga agaaagttga tgcaaatcgt ctacaagacc     1500
ggtactattt tcccaagaaa atgcaaggac ttgttcttga aggcttgtag aattggttgc     1560
tacttgtact cttctggtga tgaattcact tccccacaac aaatgatgga agatatgaag     1620
tccttggtct atgaaccatt gccaatttct ccacctgaag ctaacaatgc atctggtgaa     1680
aaaatgtcct gcgtcagtaa ctga                                            1704
```

SEQ ID NO: 11

```
MSITINLRVI AFPGHGVQSR QGIFAVMEFP RNKNTEKSSF AVKCSLSTPT DLMGKIKEKL       60

SEKVDNSVAA MATDSADMPT NLCIVDSLQR LGVEKYFQSE IDTVLDDAYR LWQLKQKDIF      120

SDITTHAMAF RLLRVKGYDV SSEELAPYAD QEGMNLQTID LAAVIELYRA AQERVAEEDS     180

TLEKLYVWTS TFLKQQLLAG AIPDQKLHKQ VEYYLKNYHG ILDRMGVRKG LDLYDAGYYK      240

ALKAADRLVD LCNEDLLAFA RQDFNINQAQ HRKELEQLQR WYADCRLDKL EFGRDVVRVS      300

NFLTSAILGD PELSEVRLVF AKHIVLVTRI DDFFDHGGPR EESHKILELI KEWKEKPAGE      360

YVSKEVEILY TAVYNTVNEL AERANVEQGR NVEPFLRTLW VQILSIFKIE LDTWSDDTAL      420

TLDDYLNNSW VSIGCRICIL MSMQFIGMKL PEEMLLSEEC VDLCRHVSMV DRLLNDVQTF      480

EKERKENTGN AVSLLLAAHK GERAFSEEEA IAKAKYLADC NRRSLMQIVY KTGTIFPRKC      540

KDMFLKVCRI GCYLYASGDE FTSPQQMMED MKSLVYEPLQ IHPPPAN                   587
```

SEQ ID NO: 12

```
atgtcaatca ccatcaacct tcgagttatc gctttcccg gccatggagt tcagagcagg        60
caaggaatat ttgcagtcat ggaatttcca aggaacaaga cacctttaa atcatccttt       120 gctgttaaat gcagcctctc tactccaaca gatttgatgg aaagataaa agaaaagttg       180 agcgagaagg ttgataattc tgtggcagcc atggctactg attctgccga tatgccact       240 aatctctgca tcgtcgactc cctccagagg ctgggagtcg aaaaatattt ccaatccgaa      300
atcgacactg ttctcgatga tgcataccgg ttatggcagc tgaagcagaa agatatattt      360
tcagacatta ctactcatgc aatggcgttt agacttctgc gagtcaaagg atacgatgtt      420
tcatcagagg agctggctcc atacgctgat caagagggca tgaacttgca aacgattgat      480
ctggcggcgg tcatcgagct gtacagagca gcacaggaga gagtggctga ggaagacagc      540
```

TABLE 3-continued

Sequences disclosed herein.

```
actcttgaga aactgtatgt ctggaccagc acctttctga agcagcagtt gctggctggc      600
gccattcctg accagaaatt gcacaaacag gtggagtact acttgaagaa ctaccacggc      660
atattagata gaatgggagt tagaaaagga ctcgacctgt atgatgctgg ctattacaag      720
gccctcaaag ctgcagatag gttggttgat ctatgcaatg aagaccttct agcatttgca      780
aggcaagatt ttaatattaa ccaagcccaa caccgcaaag aacttgagca actgcaaagg      840
tggtatgcag attgtaggtt ggacaaactc gagtttggaa gagatgtggt gcgtgtatcg      900
aattttctga cttcagccat ccttggtgat ccagagcttt ctgaagtccg tctagtgttt      960
gccaaacata ttgtgctagt gactaggata gatgatttt tcgatcatgg cgggcctaga     1020
gaagaatcac acaagatcct tgaactaata aaagaatgga agagaagcc agctggagaa     1080
tatgtttcca agaagttga gatcctatat accgcggtgt acaatacggt aaacagttg     1140
gcagagaggg caaatgttga acaagggcga atgttgaac catttctacg tacactgtgg    1200
gttcaaatac tgtcgatttt caagatagag ttggatacat ggagcgatga cacagcacta    1260
accttggatt attacttgaa caactcatgg gtgtcgattg ttgtagaat ctgcattctc     1320
atgtccatgc aattcattgg tatgaagtta ccagaagaaa tgcttctcag tgaagagtgc    1380
gttgatttgt gtaggcatgt ttccatggtc gaccgtctgc tcaatgatgt ccaaactttt    1440
gagaaggaac ggaaagaaaa tacaggaaac gctgtgagcc ttctgctagc agctcacaag    1500
ggtgaaagag ccttcagtga agaggaagcc atagcaaaag cgaaatattt ggctgactgt    1560
aacaggagaa gtctgatgca gattgtgtat aaaacaggaa ccattttccc aagaaaatgc    1620
aaagatatgt tcttgaaggt gtgcaggatt ggttgctatt tgtatgcgag tggcgacgaa    1680
tttacttccc ctcaacaaat gatggaagat atgaagtcat tagtttatga gccccctccaa   1740
attcacccctc cacctgctaa ctaa                                           1764
```

---

What is claimed is:

1. A method of producing a manoyl oxide, comprising: growing a recombinant host, comprising:
   (a) a gene encoding a geranylgeranyl diphosphate synthase (GGPPS) polypeptide,
      wherein the GGPPS polypeptide comprises a polypeptide having at least 90% sequence identity to the amino acid sequence set forth in SEQ ID NOs:2 or 4;
   (b) a gene encoding a polypeptide catalyzing formation of copal-8-ol diphosphate from qeranylgeranyl diphosphate (GGPP),
      wherein the polypeptide catalyzing formation of copal-8-ol diphosphate from GGPP comprises a polypeptide having at least 90% sequence identity to the amino acid sequence set forth in SEQ ID NO:6; and
   (c) a gene encoding a polypeptide catalyzing formation of manoyl oxide from copal-8-ol diphosphate,
      wherein the polypeptide catalyzing formation of manoyl oxide from copal-8-ol diphosphate comprises a polypeptide having at least 90% sequence identity to the amino acid sequence set forth in SEQ ID NOs:9 or 11 in a culture medium, under conditions in which the genes are expressed;
   wherein the manoyl oxide is synthesized by the host.

2. The method of claim 1, wherein the manoyl oxide is (13R) manoyl oxide.

3. A method for producing a terpenoid, comprising:
   (a) culturing a recombinant host capable of producing a manoyl oxide, comprising:
      (i) a gene encoding a geranylgeranyl diphosphate synthase (GGPPS) polypeptide,
         wherein the GGPPS polypeptide comprises a polypeptide having at least 90% sequence identity to the amino acid sequence set forth in SEQ ID NOs:2 or 4;
      (ii) a gene encoding a polypeptide catalyzing formation of copal-8-ol diphosphate from geranylgeranyl diphosphate (GGPP),
         wherein the polypeptide catalyzing formation of copal-8-ol diphosphate from GGPP comprises a polypeptide having at least 90% sequence identity to the amino acid sequence set forth in SEQ ID NO:6; and
      (iii) a gene encoding a polypeptide catalyzing formation of manoyl oxide from copal-8-ol diphosphate,
         wherein the polypeptide catalyzing formation of manoyl oxide from copal-8-ol diphosphate comprises a polypeptide having at least 90% sequence identity to the amino acid sequence set forth in SEQ ID NOs:9 or 11;
      wherein at least one of the genes is a recombinant gene;
      in a culture medium, under conditions in which the genes are expressed;
         wherein the manoyl oxide is synthesized by the recombinant host;
   (b) isolating the manoyl oxide produced by the recombinant host; and
   (c) converting the manoyl oxide into the terpenoid.

4. The method of claim 3, wherein the manoyl oxide is isolated from the recombinant host and/or from the culture medium.

5. The method of claim 3, wherein the manoyl oxide is converted into the terpenoid by organic chemical synthesis.

6. The method of claim 3, wherein the terpenoid is forskolin.

7. The method of claim 3, wherein the terpenoid is ambrox.

8. The method of claim 1, further comprising quantifying the manoyl oxide produced by the recombinant host.

9. The method of claim 1, further comprising isolating the manoyl oxide produced by the recombinant host.

10. The method of claim 3, wherein the recombinant host is a plant cell, a mammalian cell, an insect cell, a fungal cell, or a bacterial cell.

11. The method of claim 10, wherein the bacterial cell is a *Escherichia* bacteria cell, a *Lactobacillus* bacteria cell, a *Lactococcus* bacteria cell, a *Cornebacterium* bacteria cell, a *Acetobacter* bacteria cell, a *Acinetobacter* bacteria cell or a *Pseudomonas* bacterial cell.

12. The method of claim 10, wherein the fungal cell comprises a yeast cell.

13. The method of claim 12, wherein the yeast cell is a cell from *Saccharomyces cerevisiae, Schizosaccharomyces pombe, Yarrowia lipolytica, Candida glabrata, Ashbya gossypii, Cyberlindnera jadinii, Pichia pastoris, Kluyveromyces lactis, Hansenula polymorpha, Candida boidinii, Arxula adeninivorans, Xanthophyllomyces dendrorhous* or *Candida albicans* species.

14. The method of claim 12, wherein the yeast cell is a *Saccharomycete*.

15. The method of claim 12, wherein the yeast cell is a cell from the *Saccharomyces cerevisiae* species.

* * * * *